US011389089B2

(12) United States Patent
Bremer et al.

(10) Patent No.: US 11,389,089 B2
(45) Date of Patent: Jul. 19, 2022

(54) INSERTER FOR ANALYTE SENSORS

(71) Applicant: Metronom Health, Inc., Laguna Hills, CA (US)

(72) Inventors: Troy M. Bremer, Irvine, CA (US); Barry Lyons, Sutton (IE)

(73) Assignee: Metronom Health, Inc., Laguna Hills, CA (US)

( * ) Notice: Subject to any disclaimer, the term of this patent is extended or adjusted under 35 U.S.C. 154(b) by 63 days.

(21) Appl. No.: 16/606,751

(22) PCT Filed: Apr. 19, 2018

(86) PCT No.: PCT/US2018/028318
§ 371 (c)(1),
(2) Date: Oct. 19, 2019

(87) PCT Pub. No.: WO2018/195286
PCT Pub. Date: Oct. 25, 2018

(65) Prior Publication Data
US 2020/0060587 A1  Feb. 27, 2020

Related U.S. Application Data

(60) Provisional application No. 62/629,916, filed on Feb. 13, 2018, provisional application No. 62/487,038, filed on Apr. 19, 2017, provisional application No. 62/487,084, filed on Apr. 19, 2017.

(51) Int. Cl.
*A61B 5/145* (2006.01)
*A61B 5/00* (2006.01)

(52) U.S. Cl.
CPC ........ *A61B 5/14532* (2013.01); *A61B 5/1451* (2013.01); *A61B 5/6833* (2013.01); *A61B 2560/063* (2013.01)

(58) Field of Classification Search
CPC .......... A61B 2560/063; A61B 2560/06; A61B 2560/0443; A61B 5/145; A61B 5/14532;
(Continued)

(56) References Cited

U.S. PATENT DOCUMENTS 9,084,686 B1  7/2015 McLean et al.
2005/0149057 A1  7/2005 Rathert
(Continued)

FOREIGN PATENT DOCUMENTS

GB     2 307 280 A    5/1997
GB     2 312 932 B    12/1997
WO     2016012482 A1  1/2016
WO     WO-2016130679 A2 *  8/2016 ........ A61M 5/14248

OTHER PUBLICATIONS

Extended European Search Report dated Dec. 9, 2020 for European Patent Application 18788619.7.
International Search Report for PCT/US2018/028318 dated Jun. 19, 2018.
First Office Action dated Jun. 3, 2021 Chinese Patent Application No. 201880030844.7.

*Primary Examiner* — Eric F Winakur
*Assistant Examiner* — Alice Ling Zou
(74) *Attorney, Agent, or Firm* — Knobbe Martens Olson & Bear, LLP

(57) ABSTRACT

An inserter for a medical device, where the inserter includes a housing having a first end with an opening therein, an actuator connected to a first gear, an actuator biasing element, a cam gear assembly including a cam member and a second gear, a cam bridge follower in contact with the cam member, and a first plunger assembly having a first plunger and a first biasing element.

17 Claims, 20 Drawing Sheets

(58) Field of Classification Search
CPC .......... A61B 5/14546; A61B 5/150053; A61B 5/150969; A61B 5/15101; A61B 5/15103; A61B 5/15115; A61B 5/151; A61B 5/14503–1451; A61B 5/1486–14865; A61B 5/6833; A61B 5/15105; A61B 5/15113; A61B 5/15126–15132; A61B 5/15117; A61B 5/15186–15192; A61B 5/15196; A61B 5/157; A61M 5/002; A61M 5/003; A61M 5/158; A61M 5/20; A61M 2005/1585; A61M 2005/2026; A61M 2005/206; A61M 5/14248; A61M 2005/14252

See application file for complete search history.

(56) References Cited

U.S. PATENT DOCUMENTS

| | | |
|---|---|---|
| 2008/0027461 A1 | 1/2008 | Vaquero et al. |
| 2008/0195045 A1* | 8/2008 | Lanigan ........... A61B 5/150175 604/117 |
| 2010/0217105 A1 | 8/2010 | Yodfat et al. |
| 2011/0061660 A1 | 3/2011 | Cruzada et al. |
| 2012/0010642 A1* | 1/2012 | Lee .................... A61B 5/14546 606/182 |
| 2012/0190951 A1 | 7/2012 | Curry et al. |
| 2014/0074138 A1 | 3/2014 | Kan |
| 2015/0273151 A1 | 10/2015 | McLoughlin et al. |
| 2017/0112534 A1* | 4/2017 | Schoonmaker ...... A61B 5/0004 |

* cited by examiner

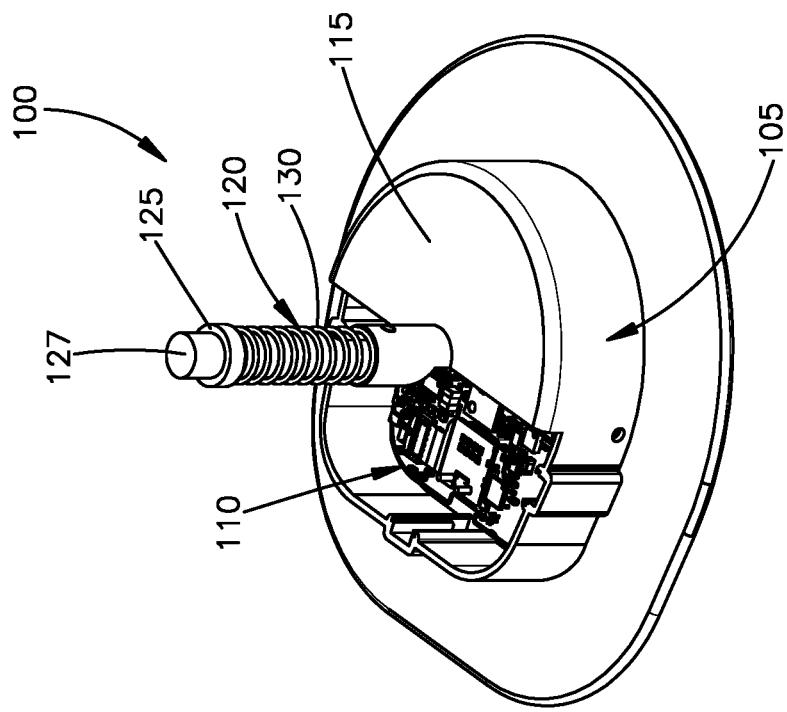
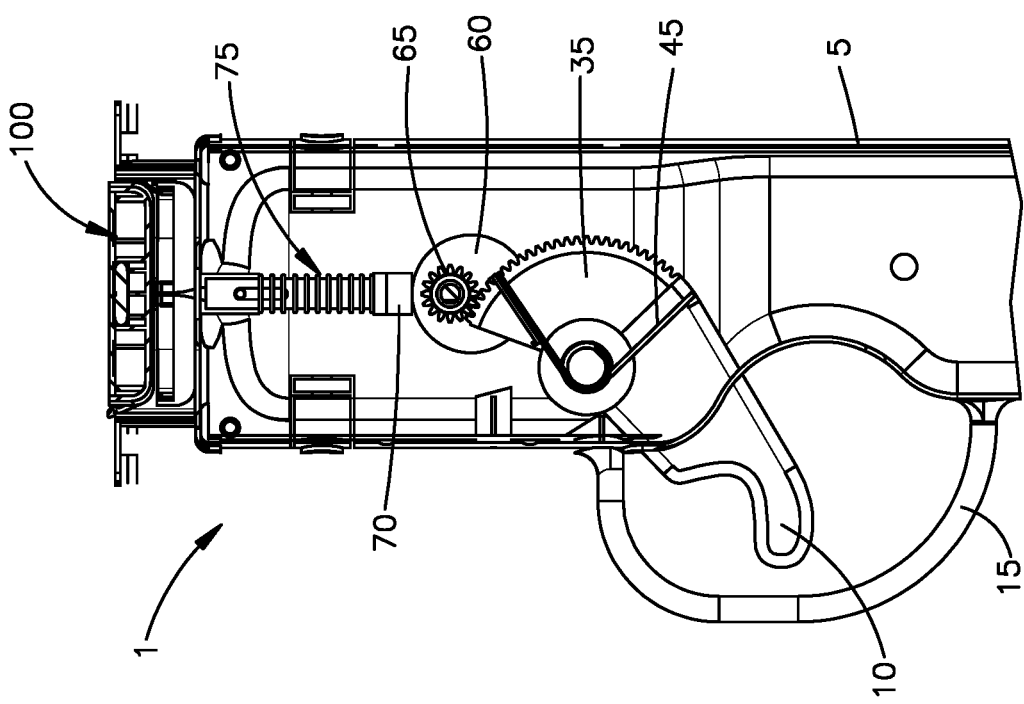

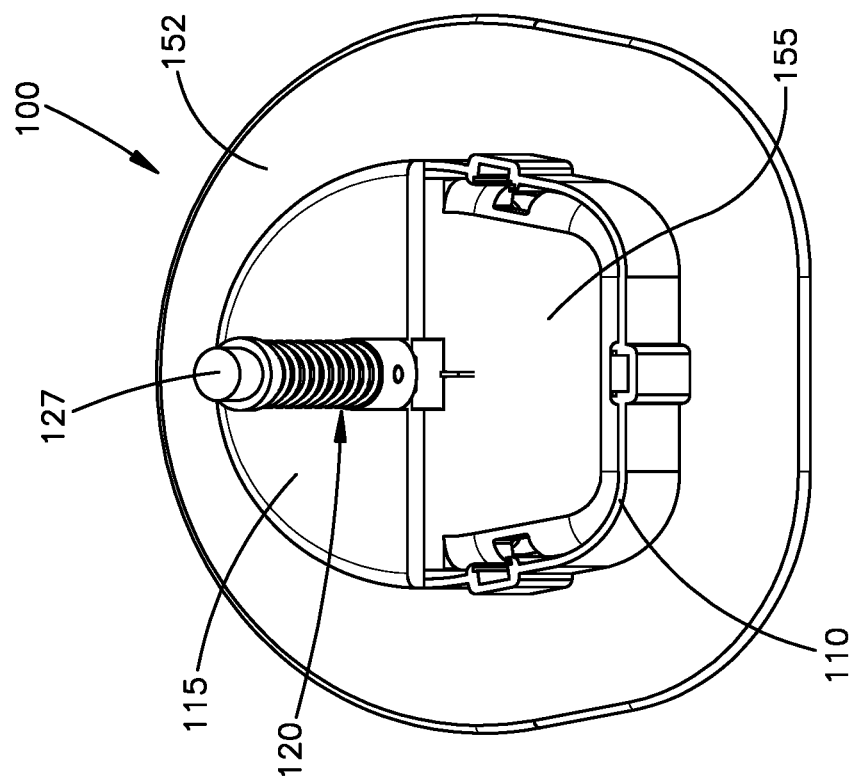
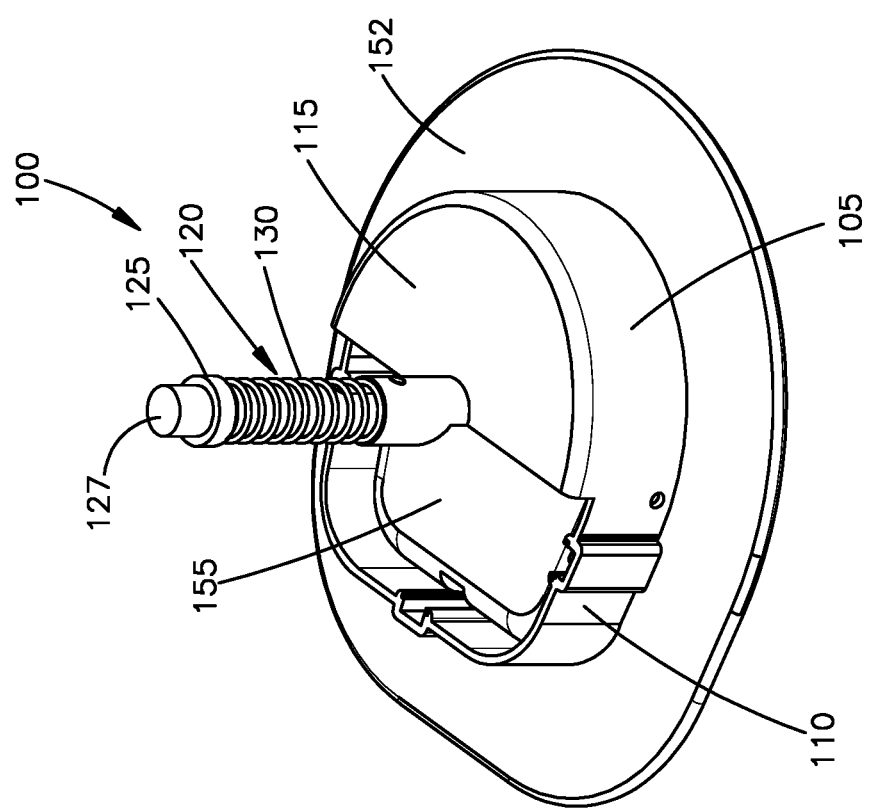

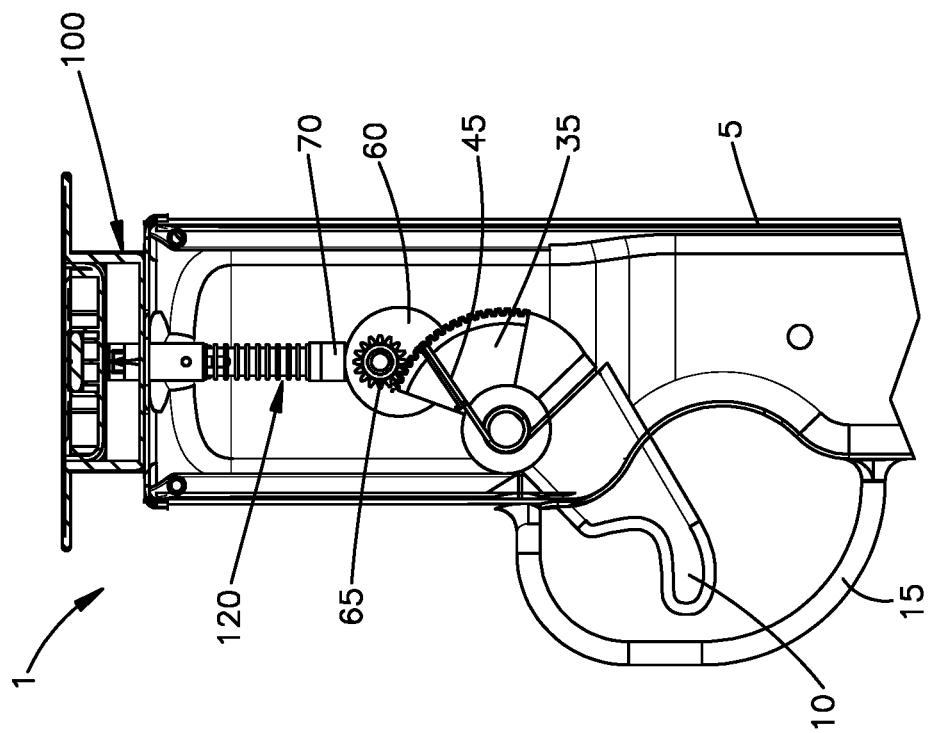
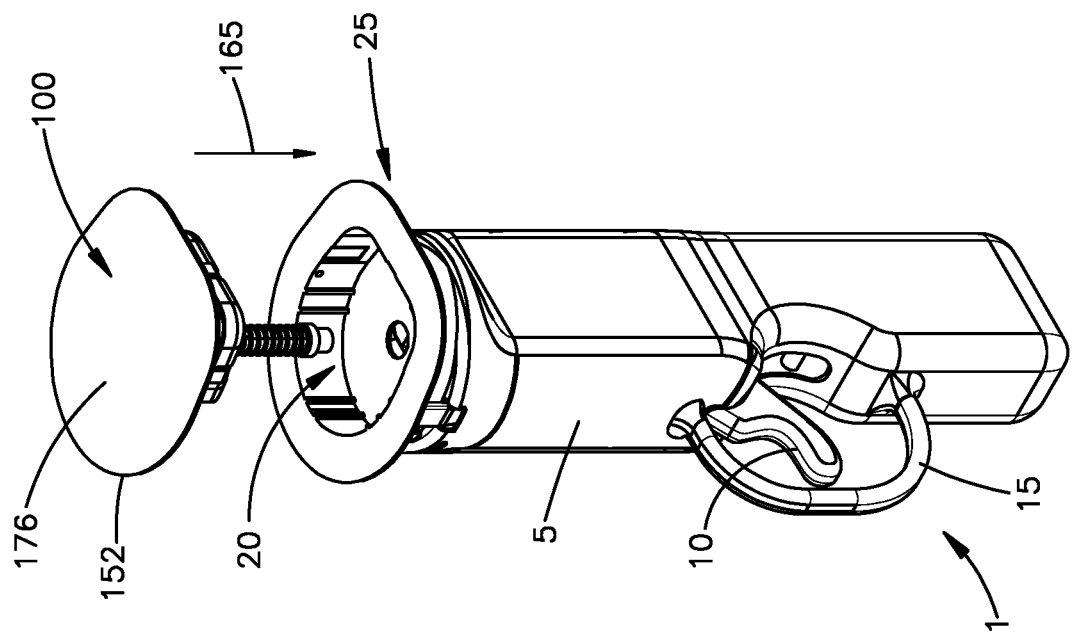

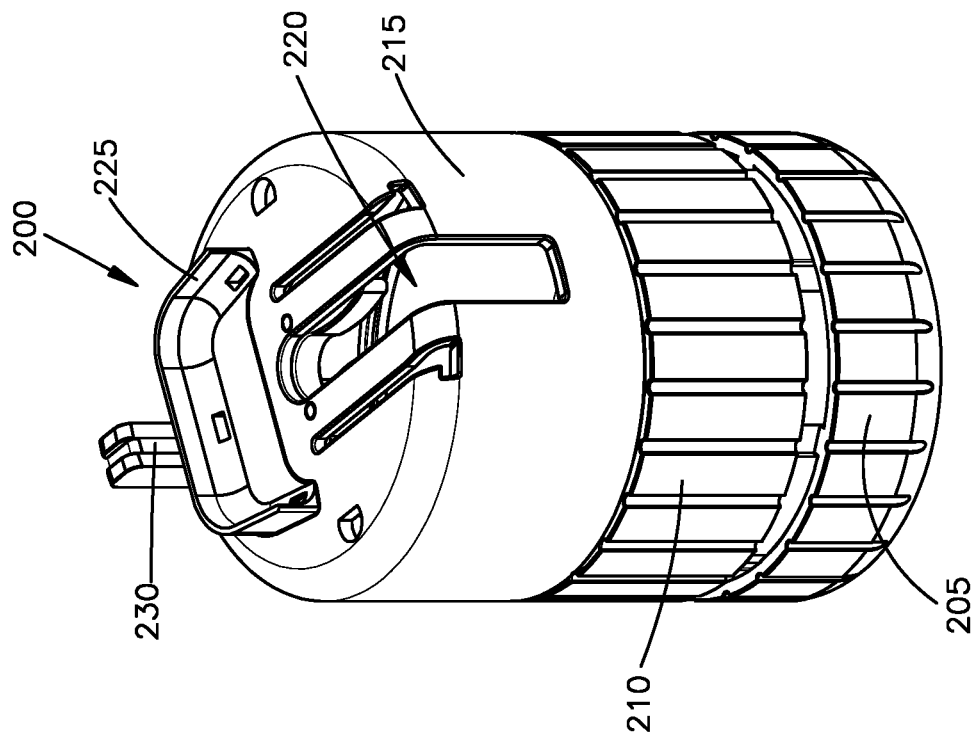
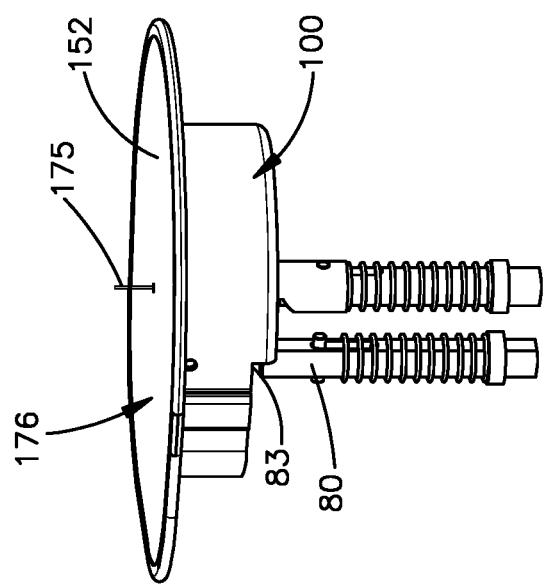

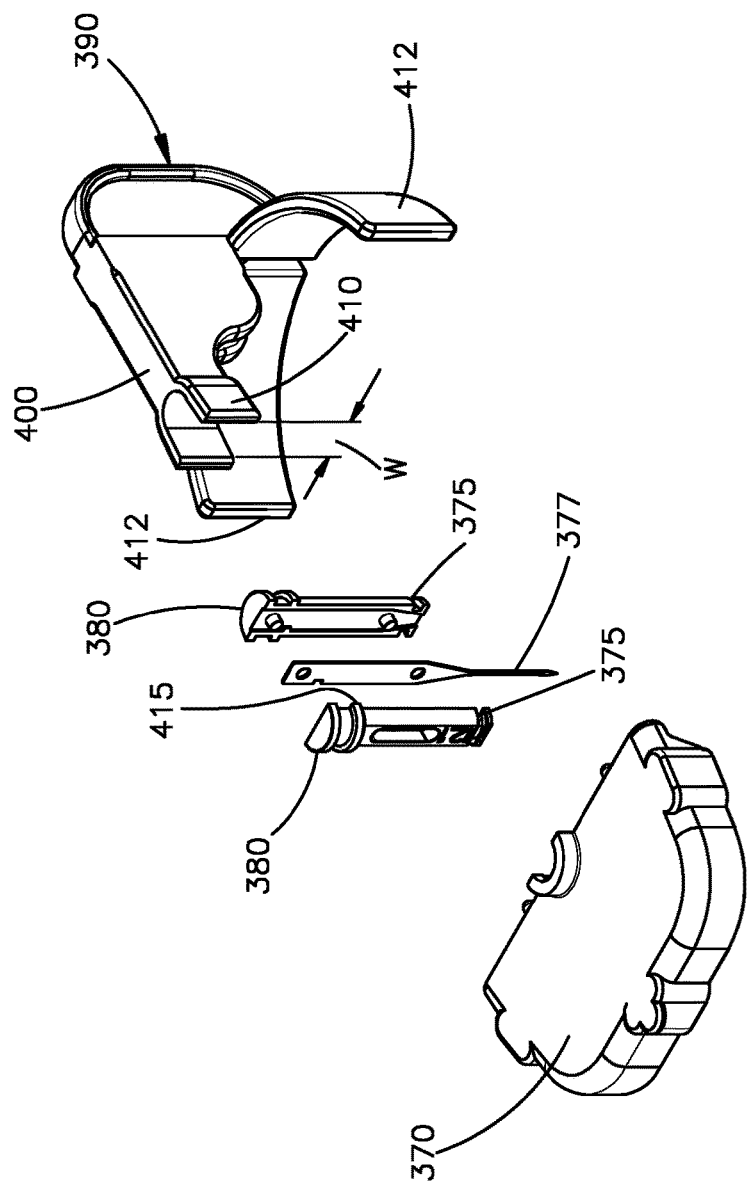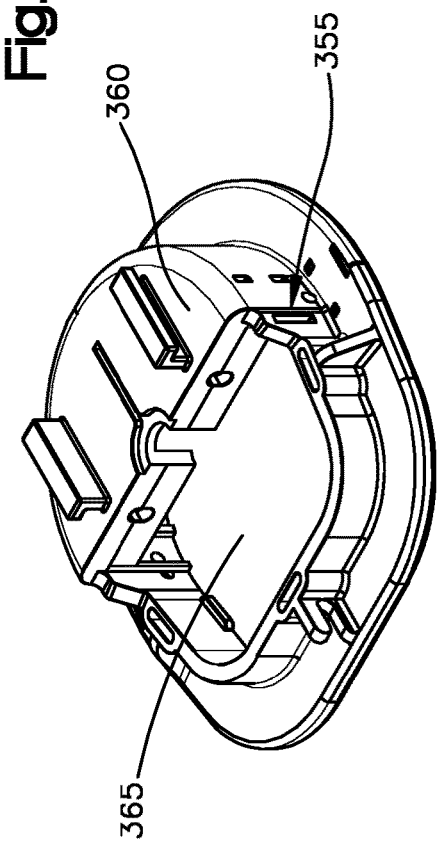
Fig.21

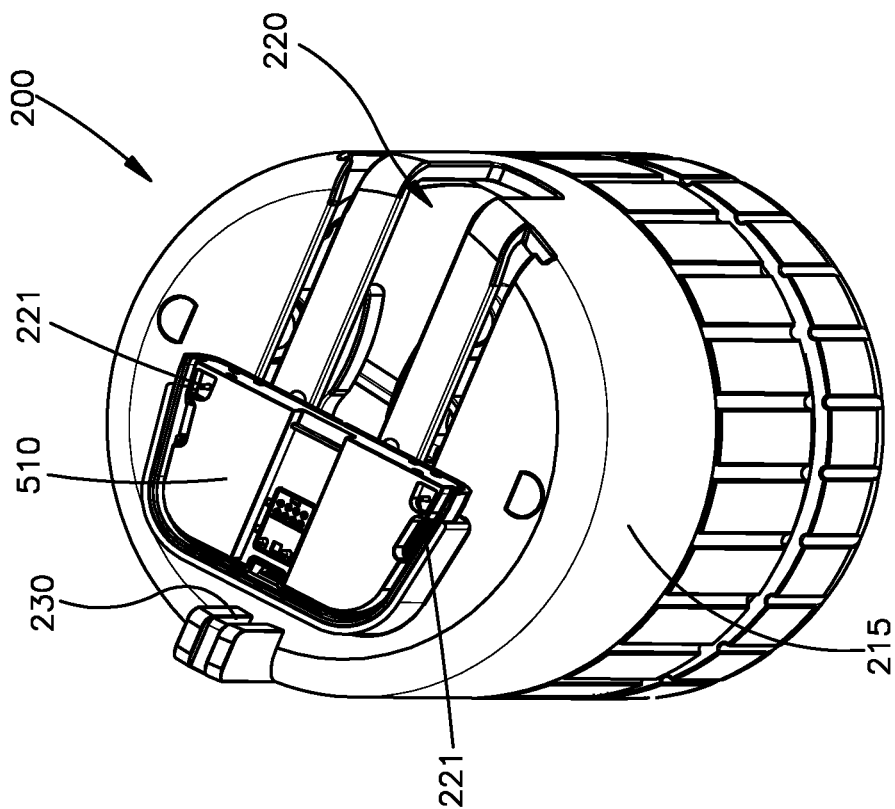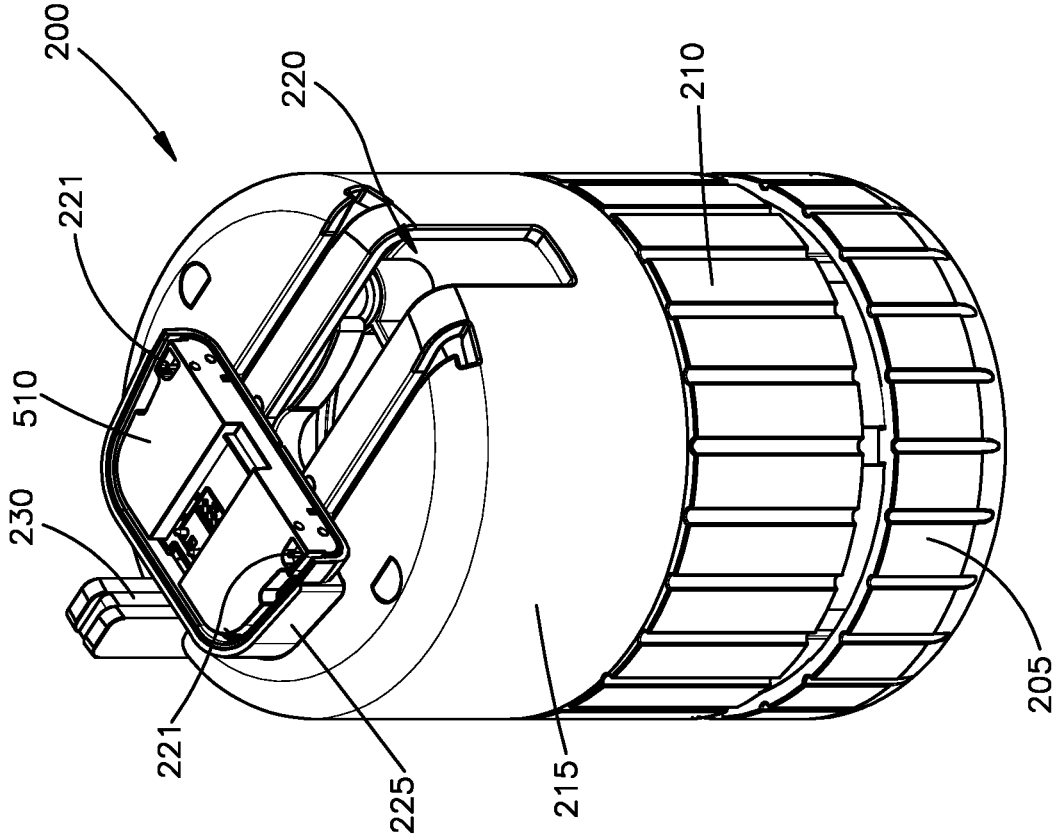

INSERTER FOR ANALYTE SENSORS

RELATED APPLICATIONS

This application is a National Stage Entry Application of PCT/US2018/028318, filed Apr. 19, 2018, which claims the benefit of U.S. Provisional Application No. 62/629,916, filed Feb. 13, 2018, U.S. Provisional Application No. 62/487,038, filed Apr. 19, 2017, and U.S. Provisional Application No. 62/487,084, filed Apr. 19, 2017, the entire contents of each of these applications are incorporated herein by reference.

BACKGROUND

Field

The disclosed and described technology relates generally to inserters for inserting or delivering components/structures of medical devices, such as, for example, sensing elements of analyte sensors, into the skin of a patient, in order to provide interstitial fluid measurements of an analyte.

Description of the Related Technology

Diabetes is a disease of insufficient blood glucose regulation. In non-diabetic people, the body's beta cells monitor glucose and deliver just the right amount of insulin on, for example, a minute-by-minute basis for tissues in the body to uptake the right amount of glucose, keeping blood glucose at healthy levels. In diabetic patients, this regulation primarily fails due to: (1) insufficient insulin production and secretion, and/or (2) a lack of normal sensitivity to insulin by the tissues of the body. Glucose sensors can be used to monitor glucose levels in diabetic patients allowing proper dosing of diabetic treatments, including, for example, insulin.

More generally, analyte tracking and monitoring enable improved monitoring, diagnosis, and treatment of diseases, including diabetes. Existing methods to measure, monitor, and track analyte levels, may include sampling a bodily fluid, preparing the sample for measurement, and estimating the analyte level in the sample. For example, a diabetic may prick a finger to obtain a blood sample to measure glucose in a glucose monitoring unit. Such existing methods may be painful, unpleasant or inconvenient for the patient, resulting in lower compliance with physician orders to, for example, take glucose readings at certain times each day or based on patient activity. Moreover, effective monitoring, diagnosis, and treatment may benefit from fusing multiple sensor readings that measure different aspects of a patient's state. Readings from one or more analyte sensors, as well as other bio sensor systems and/or activity sensors may be combined with past readings to determine results that characterize a patient's state, and may be used to monitor, diagnose, and treat a patient. For example, an alarm may be triggered if a patient's glucose level exceeds a threshold.

Accordingly, there is a need for analyte sensors (1) that do not require unpleasant blood draws or sample preparation if measurements are to be taken multiple times each day, (2) to be sufficiently selective, sensitive, and to provide repeatable and reproducible measurements, and (3) that are stable with low drift. There is also a need for an inserter that can be used to easily and painlessly deliver the sensor's sensing element transdermally.

Analyte sensors, such as glucose sensors, can produce a digital electronic signal that depends on the concentration of a specific chemical or set of chemicals (analyte) in bodily fluid or tissue. The sensor usually includes two main components, (1) a chemical or biological part that reacts or complexes with the analyte in question to form new chemical or biological products or changes in energy that can be detected by means of the second component and (2) a transducer.

The disclosed technology integrates an innovative analyte sensor, controlled by a controller, with embodiments of a reusable inserter that can be used to transdermally deliver the analyte sensor's sensing element with little to no pain

SUMMARY

Methods and systems are disclosed for an inserter system for a minimally invasive tissue implant. As will be readily apparent to those skilled in the art, the methods and inserted systems disclosed herein are equally applicable for use with, for example, biosensors, micro catheters and drug eluting implants. In some embodiments, the inserter system is for use with as continuous glucose monitoring system. In one example, the system for sensor implantation can include an inserter and a sensor. The inserter can include a lancet tip that includes a convex feature attached to a first surface of the lancet tip. The inserter can also include an inset on either side of the lancet tip. The sensor can include a distal end that is configured to form a loop. The loop is configured to pass around the insets of the lancet tip, with a portion of the loop positioned adjacent the convex feature.

An embodiment of the invention is directed to an inserter for a medical device, where the inserter includes a housing having a first end with an opening therein, an actuator connected to a first gear, an actuator biasing element, a cam gear assembly comprising a cam member and a second gear, a cam bridge follower in contact with the cam member, and a first plunger assembly comprising a first plunger and a first biasing element.

In another embodiment, the invention is directed to an inserter for a medical device, where the inserter comprises a housing having a first end with an opening therein, an actuator connected to a first gear, an actuator biasing element, a cam gear assembly comprising a cam member and a second gear, a cam bridge follower in contact with the cam member, and a first plunger assembly comprising a first plunger and a first biasing element. The inserter also includes a tub assembly that comprises a tub portion including a first portion that includes a first component of the medical device, a second portion capable of holding a second component of the medical device and a base, and a second plunger assembly comprising a second plunger and a second biasing element.

Embodiments of the invention are also directed to a tub assembly for use with a medical device inserter. In these embodiments, the tub assembly includes a tub portion that has a first portion that includes at least a first component of the medical device, a second portion capable of holding at least a second component of the medical device, a base, and a plunger assembly comprising a plunger, a biasing element and a skin piercing element.

An inserter for a medical device is disclosed. In some embodiments, the inserter composes a housing that having a first portion that includes a slot therein and a component holder for a component of the medical device, a second portion that is rotatable relative to the first portion and that includes a cam element on its interior, a third portion attached to the second portion and longitudinally slideable relative to the second portion and a spring element disposed between the second portion and the third portion, a first plunger assembly comprising a first plunger having a first end and a second end that includes a keyed portion, and a first biasing element, a second plunger assembly comprising a second plunger having a first end and a second end, and a second biasing element and a plunger bridge connected to the first end of the first plunger and the first end of second plunger, wherein at least a portion of a bottom surface of the plunger bridge contacts the cam element.

Embodiments of the present invention also include inserter for a medical device. In some embodiments, the inserter comprises a housing that having a first portion that includes a slot therein and a component holder for a component of the medical device, a second portion that is rotatable relative to the first portion and that includes a cam element on its interior, a third portion attached to the second portion and longitudinally slideable relative to the second portion and a spring element disposed between the second portion and the third portion, a first plunger assembly comprising a first plunger having a first end and a second end that includes a keyed portion, and a first biasing element, a second plunger assembly comprising a second plunger having a first end and a second end, and a second biasing element and a plunger bridge connected to the first end of the first plunger and the first end of second plunger, wherein at least a portion of a bottom surface of the plunger bridge contacts the cam element. In some embodiments, the cam element includes two cam lobes that define two low points and two high points on the cam element such that when the second portion is rotated relative to the first portion, the bottom surface of the plunger bridge that contacts the cam element slides along the cam element and moves up and down within an interior of the inserter a distance that corresponds to a profile of the cam lobes. Accordingly, the first plunger and the second plunger move up and down within the interior of the inserter in a manner that corresponds to the movement of the plunger bridge.

Further, disclosed is an inserter for a medical device where the inserter comprises a housing comprising a first portion that includes a slot therein and a component holder for a component of the medical device, a second portion that is rotatable relative to the first portion and that includes a cam element on its interior, a third portion attached to the second portion and longitudinally slideable relative to the second portion, and a spring element disposed between the second portion and the third portion. The inserter also includes a first plunger assembly comprising a first plunger having a first end and a second end that includes a keyed portion, and a first biasing element, a second plunger assembly comprising a second plunger having a first end and a second end, and a second biasing element, a plunger bridge connected to the first end of the first plunger and the first end of second plunger, wherein at least a portion of a bottom surface of the plunger bridge contacts the cam element; and a tub assembly that comprises a tub portion including a first portion that includes a first component of the medical device, a second portion capable of holding a second component of the medical device and a base. The tub assembly further includes a piercing element plunger comprising a piercing element, a flange portion, and a locking portion; a safety tab that comprises a locking arm including an engaging portion that engages a portion of the piercing element plunger, a tub engaging portion, and a grasping portion; and a removeable lid, wherein the piercing element plunger is inserted into the slot in the first portion of the inserter, and wherein the flange portion of the piercing element plunger is received within the keyed portion of the first plunger.

In some embodiments, a kit for applying a medical device to a patient's skin is provided. The kit comprises an inserter comprising a housing having a first portion that includes a slot therein and a component holder for a component of the medical device, a second portion that is rotatable relative to the first portion and that includes a cam element on its interior, a third portion attached to the second portion and longitudinally slideable relative to the second portion, and a spring element disposed between the second portion and the third portion; a first plunger assembly comprising a first plunger having a first end and a second end that includes a keyed portion, and a first biasing element; a second plunger assembly comprising a second plunger having a first end and a second end, and a second biasing element; a plunger bridge connected to the first end of the first plunger and the first end of second plunger, wherein at least a portion of a bottom surface of the plunger bridge contacts the cam element; and a tub assembly. The tub assembly comprises a tub portion including a first portion that includes a first component of the medical device, a second portion capable of holding a second component of the medical device and a base, a piercing element plunger comprising a piercing element, a flange portion and a locking portion; a safety tab comprising a locking arm including an engaging portion that engages a portion of the piercing element plunger, a tub engaging portion and a grasping portion; and a removeable lid.

Also disclosed is a tub assembly comprising a tub portion including a first portion that includes a first component of the medical device, a second portion capable of holding a second component of the medical device and a base; a piercing element plunger comprising a piercing element, a flange portion, and a locking portion; a safety tab comprising a locking arm including an engaging portion that engages a portion of the piercing element plunger, a tub engaging portion and a grasping portion; and a removeable lid.

In some embodiments, the invention is directed to a kit for applying a medical device to a patient's skin where the kit comprises an inserter including a housing having a first end with an opening therein, an actuator connected to a first gear, an actuator biasing element; a cam gear assembly comprising a cam member and a second gear, a cam bridge follower in contact with the cam member, a first plunger assembly comprising a first plunger and a first biasing element and a tub assembly. In certain embodiments, the tub assembly comprises a tub portion including a first portion that includes a first component of the medical device, a second portion capable of holding a second component of the medical device and a base, and a second plunger assembly comprising a second plunger and a second biasing element.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following FIGS. may not be drawn to scale.

FIG. 3 is a side view of an inserter showing the internal components, according to an embodiment of the present invention;

FIG. 4 is a perspective view of a sterile tub assembly, according to an embodiment of the present invention;

FIG. 7 is a perspective view of a sterile tub assembly, according to an embodiment of the present invention;

FIG. 8 is a top view of the sterile tub assembly depicted in FIG. 8, according to an embodiment of the present invention;

FIG. 9 is a perspective view of an inserter showing insertion of sterile tub assembly, according to an embodiment of the present invention;

FIG. 10 is a side view of the inserter and sterile tub assembly depicted in FIG. 10 with the sterile tub assembly fully inserted into the inserter, according to an embodiment of the present invention;

FIG. 13 depicts a magnified view of the tub assembly of FIG. 10 in the actuated state of FIG. 12, according to an embodiment of the present invention;

FIG. 14 is a perspective view of an inserter, according to an embodiment of the present invention;

FIG. 21 is an exploded view of the tub assembly depicted in FIG. 20, according to an embodiment of the present invention;

FIG. 29A is a perspective view of the inserter depicted in FIG. 14 with a transmitter included thereon, according to an embodiment of the present invention;

FIG. 29B is another perspective view of the inserter depicted in FIG. 14 with a transmitter included thereon, according to an embodiment of the present invention;

DETAILED DESCRIPTION

Figure 2:
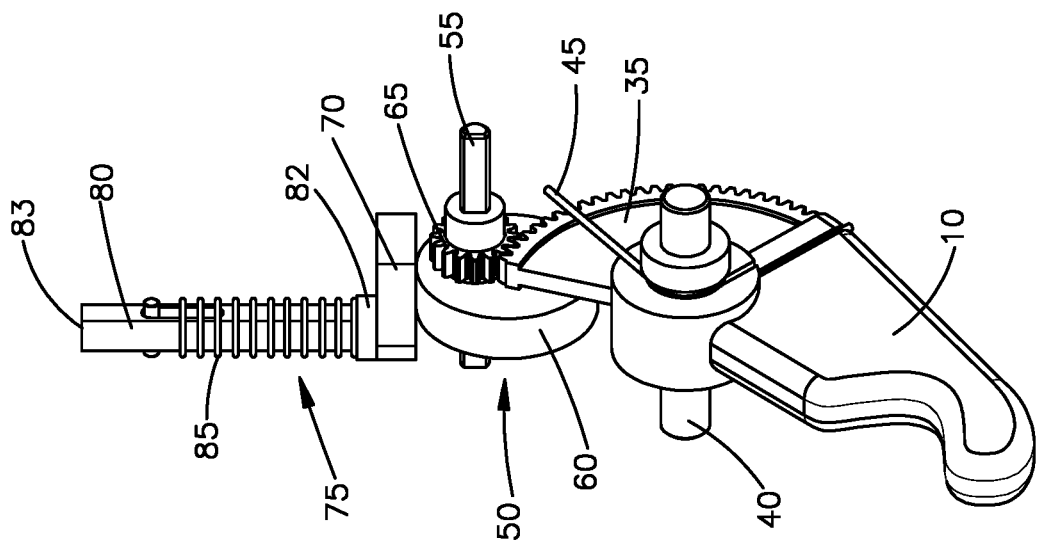
FIG. 2 depicts the internal components of the inserter of FIG. 1, according to an embodiment of the present invention.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will also be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

All existing subject matter mentioned herein (e.g., publications, patents, patent applications and hardware) is incorporated by reference herein in its entirety except insofar as the subject matter may conflict with that of the present invention (in which case what is present herein shall prevail).

Embodiments of the disclosed and described technology relate to inserters that may be used to deliver components of a medical device transdermally. Example medical devices that can be used with the disclosed and described technology include, and are not limited to, body wearable devices such as analyte sensors, pumps for the delivery of therapeutic drugs (insulin, chemotherapy drugs, etc.), and any other device as will be readily understood by those of skill in the art. Example medical device components that can be delivered transdermally with the embodiments disclosed and described herein include, and are not limited to, analyte sensing elements, drug delivery cannulas (micro catheters) or other delivery lumens for infusion pumps to deliver, for example, insulin and other therapeutic agents/treatments to a patient, etc. Additional items that can be delivered with the embodiments of the inserters disclosed herein include, and are not limited to, drug eluting implants. For analyte sensors, example analytes that can be measured using the embodiments of e invention disclosed and described herein include, and are not limited to, glucose, galactose, fructose, lactate, peroxide, cholesterol, amino acids, alcohol, lactic acid, and mixtures of the foregoing.

Analyte sensors that may be used with the embodiments of the disclosed and described technology include, and are not limited to, those described in the following commonly-assigned U.S. patent applications and International Patent Applications: U.S. patent application Ser. No. 15/254,995, entitled "SYSTEMS AND METHODS FOR CONTINUOUS HEALTH MONITORING USING AN OPTO-ENZYMATIC ANALYTE SENSOR," filed Sep. 1, 2016 by Troy Bremer; U.S. patent application Ser. No. 15/754,271, entitled "SYSTEMS AND METHODS FOR CONTINUOUS HEALTH MONITORING USING AN OPTO-ENZYMATIC ANALYTE SENSOR," filed Feb. 21, 2018 by Troy Bremer; and International Patent Application No. PCT/US18/20228, entitled "ANALYTE SENSORS AND METHODS OF MANUFACTURING ANALYTE SENSORS," filed Feb. 28, 2018 by Troy Bremer, et al., the contents of each of the above-identified patent applications are incorporated herein by reference in their entireties for all purposes.

The inserters disclosed and described herein are reusable and may be used many times by a user to transdermally deliver the relevant device components and to attach the devices to a user's/patient's skin. Such a reusable inserter reduces the costs for the medical devices that are used with the reusable inserters.

Figure 1:
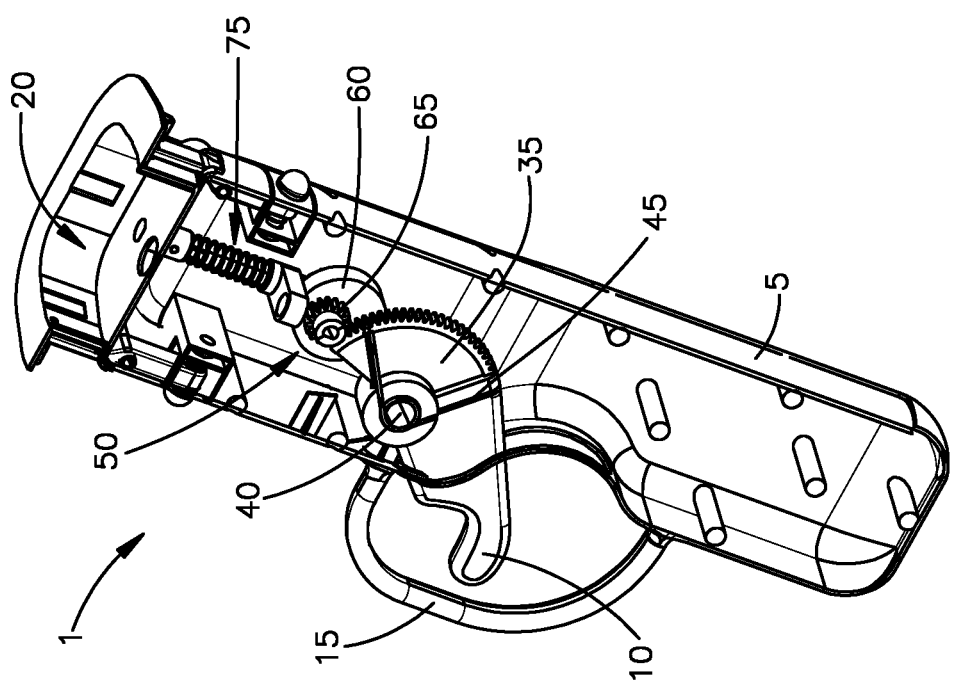
FIG. 1 is a perspective view of an inserter showing the internal components, according to an embodiment of the present invention.

Depicted in FIG. 1 is an inserter 1 according to an embodiment of the invention. As can be seen in the figure, a portion of the housing 5 is cut away in order for the internal components to be viewed. In this embodiment, the inserter 1 includes a housing 5, a trigger 10, a trigger guard 15 and an opening 20 in a first end 25 to receive a sterile tub assembly (discussed in detail below).

As can best be seen in FIGS. 1-3, in this embodiment, the internal components of the inserter 1 include a trigger gear 35 disposed on a shaft 40 and connected to the trigger 10, a trigger biasing element 45, which, in some embodiments is a torsional spring, a cam gear assembly 50 that includes a shaft 55, a cam 60 and a cam gear 65, a cam bridge follower 70 that is in contact with the cam 60, and a transmitter plunger assembly 75 that includes a transmitter plunger 80 and a transmitter plunger biasing element 85, which, in some embodiments, is a coiled compression spring. The transmitter plunger 80 includes a first end 82 connected to the cam bridge follower 70 and a second end 83.

In some embodiments, the inserter 1 is used to transdermally deliver the percutaneous sensing element of an analyte sensor into tissue. In these embodiments, the analyte sensor can be included in sterile packaging such as, for example, a sterile tub assembly 100 as depicted in FIG. 4. The sterile tub assembly 100 includes a sterile portion 105 that contains the sterile components of the analyte sensor and a non-sterile portion 110 that is a cavity to receive a reusable transmitter (discussed in more detail below) for the analyte sensor. As can be seen in FIG. 4, the sterile tub assembly 100 also includes a cover 115 that protects the sterile components of the analyte sensor within the sterile portion 105 of the sterile tub assembly 100, a lancet plunger assembly 120 that includes a lancet plunger 125 having a free end 127 and a lancet plunger biasing element 130, which, in some embodiments, is a coiled compression spring.

Figure 6:
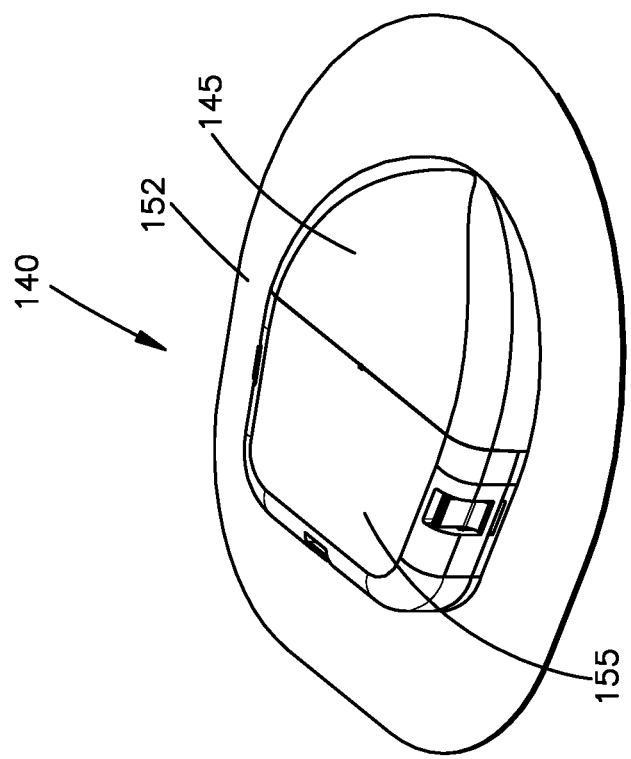
FIG. 6 is a perspective view of an analyte sensor, according to an embodiment of the present invention.
Figure 5:
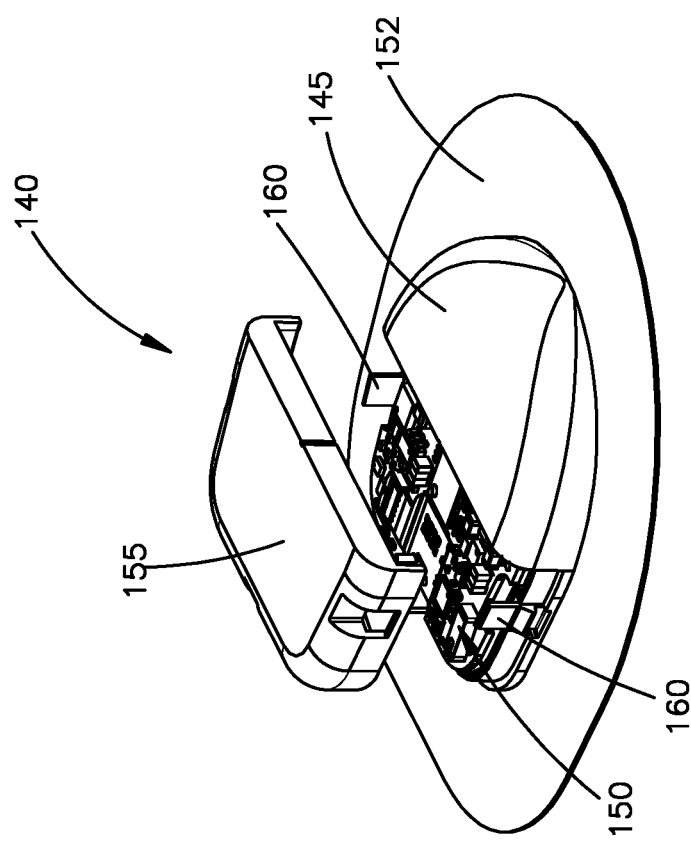
FIG. 5 is a perspective view of an analyte sensor, according to an embodiment of the present invention.

Depicted in FIGS. 5 and 6 is an embodiment of an analyte sensor 140 that can be used with the inserter 1. The analyte sensor 140 includes a sterile or first portion 145 that houses many of the components of the sensor including the battery, etc., the transmitter 150, and a transmitter or second portion 150 that receives/houses the transmitter 155, which may or may not be reusable. A plurality of attachment elements 160 may also be included to secure the transmitter 150 to the analyte sensor 140. An adhesive pad 152 is attached/adhered to the bottom of the analyte sensor 140 and sterile tub assembly 100 in such a manner that sterility is maintained within the sterile portion 105 of the sterile tub assembly 100 and the adhesive pad 152 detaches from the sterile tub assembly 100 and remains attached to the analyte sensor 140 after the inserter 1 applies the analyte sensor 140 to the skin as described below. As can be seen in FIGS. 5 and 6, prior to use, a user inserts the transmitter 155 into the transmitter or second portion 150.

Figure 11:
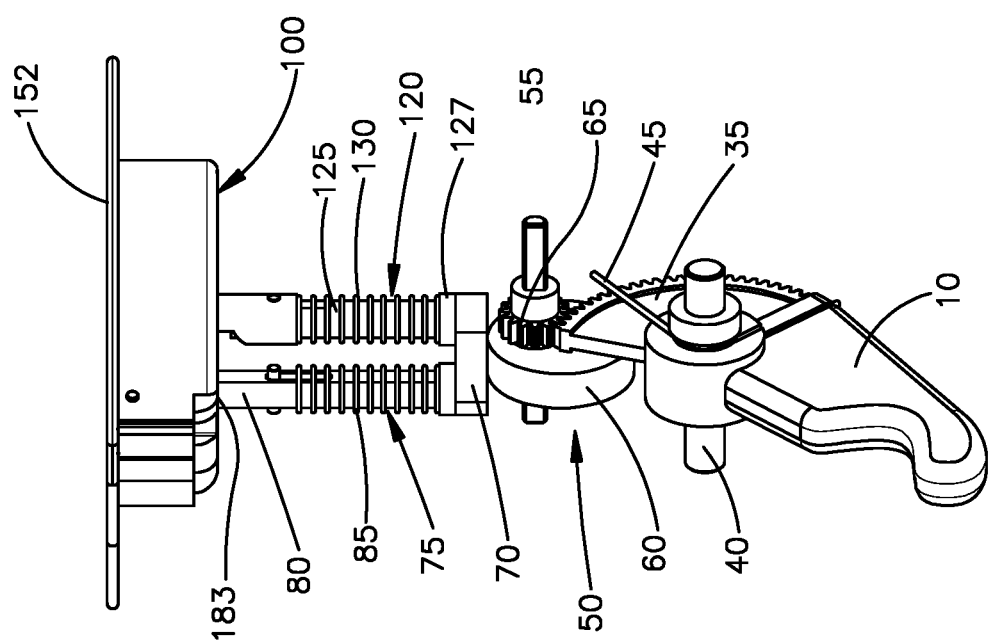
FIG. 11 depicts the internal components of the inserter shown in FIG. 10 in an un-actuated state, according to an embodiment of the present invention.

Use and operation of the inserter 1 according to an embodiment of the invention will now be described in detail. In some embodiments, the sterile tub assembly 100 will be preloaded with the analyte sensor 140 in the sterile or first portion 105 of the sterile tub assembly 100. Prior to attaching the sterile tub assembly 100 to the inserter 1, as depicted in FIGS. 7 and 8, the transmitter 155 is inserted into the transmitter or second portion 110 of the sterile tub assembly 100 and secured in place. After the transmitter 155 is in place, as depicted in FIG. 9, the sterile tub assembly 100 is inserted into the opening 20 in the first end 25 of the inserter 1 in the direction of arrow 165. As depicted in FIGS. 10 and 11, when the sterile tub assembly 100 is fully inserted into the opening 20 in the first end 25 of the inserter 1, the second end 83 of the transmitter plunger 80 either contacts or is adjacent to the transmitter 155 disposed in the sterile tub assembly 100 and the free end 127 of the lancet plunger 125 is seated within a cavity/recessed portion of the cam bridge follower 70. The inserter 1 is now ready to (a) activate the analyte sensor 140 for use, (2) attach the analyte sensor 140 to skin and (c) transdermally deliver the sensing element of the analyte sensor 140.

Prior to use, the adhesive backing is removed from the adhesive pad 152 to expose the adhesive used to adhere the adhesive pad 152 and hence, the analyte sensor 140, to a patient's skin. Next, the user/patient selects a location on the body for sensor placement and with the inserter I in hand, presses the adhesive pad 152 against the user's skin at the preferred body location. Once pressure has been applied to the adhesive pad 152 via the inserter 1, the user then, with a fast movement, pulls the trigger 10 with a finger. When pulled, the trigger 10 moves the trigger gear 35 in a corresponding manner. Because the teeth/cogs on the trigger gear 35 mesh with the teeth/cogs on the cam gear 65, rotational motion imparted on the trigger gear 35 through movement of the trigger 10 is transmitted to the cam gear 65. The rotating cam gear 65 causes the attached cam 60 to rotate in a corresponding manner. Because of the cam's eccentricity, as the cam 60 rotates, it acts on the cam bridge follower 70 thereby pushing the cam bridge follower 70, the transmitter plunger assembly 75 and the lancet plunger assembly 120 that contact the cam bridge follower 70 in a linear movement towards the sterile tub 100.

Figure 12:
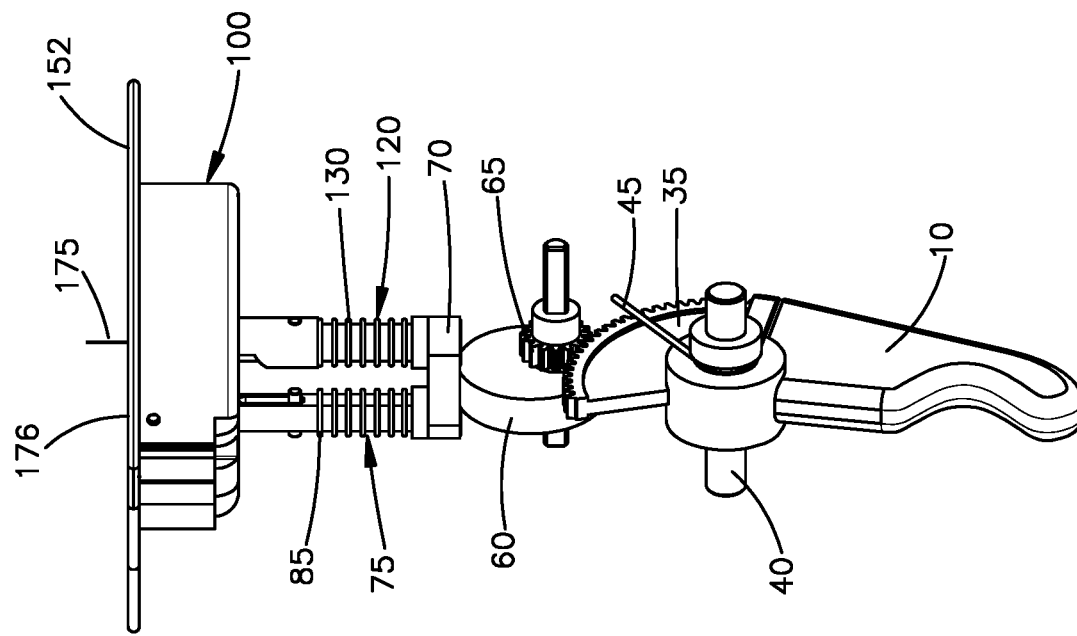
FIG. 12 depicts the internal components of the inserter shown in FIG. 10m an actuated state, according to an embodiment of the present invention.

Attached to the lancet plunger 125 is a lancet or other skin piercing element 175. Attached to the lancet 175 is the sensing element for the analyte sensor that is to be delivered transdermally. Rotation of the cam 60 pushes the cam bridge follower 70, the transmitter plunger 80 and the lancet plunger 125 through a linear movement of approximately 6.5 mm. This movement causes the lancet plunger 130 and the attached lancet 175 and sensing element to move a corresponding distance thereby piercing through the base 176 of the analyte sensor 140 and the adhesive pad 152 as depicted in FIGS. 12 and 13. Continued linear movement of the lancet 175 through the approximately 6.5 mm distance causes the lancet 175 with the sensing element attached, to pierce the user's skin thereby inserting/delivering the sensing element transdermally. This movement also causes the transmitter plunger 80 to move a corresponding distance thereby pushing the transmitter 150 that has been loaded into the transmitter or second portion 110 of the sterile tub assembly 100 in place onto the back of the analyte sensor 140. As the transmitter 155 is pushed into its working position by the plunger 80, the battery contacts on the transmitter 155 and the battery contacts for the battery included with the analyte sensor 140 align and make contact thereby activating the transmitter 155 for use. FIG. 12, depicts the state of the components of the inserter I and the sterile tub assembly 100 upon full actuation of the trigger 10. As can be seen, the transmitter plunger biasing element 85 and the lancet plunger biasing element 130 are compressed thereby loading the biasing elements 85, 130 with stored energy.

Upon release of the trigger 10, the trigger spring 45 returns the trigger 10 to its starting position, which also rotates the cam 60 back to its starting position. Rotation of the cam 60 with the aid of the biasing elements 85, 130 unloading the stored energy, causes the cam bridge follower 70, the transmitter plunger 80 and the lancet plunger 125 to retract/move back through a linear movement to their starting positions. As the lancet plunger 125 retracts, the attached lancet retracts from the patient's skin. As the lancet retracts from the skin, the sensing element detaches from the lancet 175 and is left implanted in place within the patient's skin. After the lancet 175 is fully retracted, the lancet 175 is retained within the sterile tub assembly 100 in a locked, "safe" position to prevent injury to the user, patient or anyone else. The sterile tub assembly 100 can then be disposed of safely.

The analyte sensor 140 now activated and attached to the patient's skin by way of the adhesive pad 152 can be used for approximately two (2) weeks after which, the patient can remove the analyte sensor 140 from the skin by peeling the adhesive pad 152 off of the skin. Removing the analyte sensor also removes the sensing element from the user's skin. Once the analyte sensor 140 is removed, the user can eject the reusable transmitter 155 from its clipped-on location on the analyte sensor 140. The used analyte sensor 140 can then be disposed of safely by the user and the reusable transmitter 155 can be inserted into a new sterile tub assembly 100 for use with a new analyte sensor 140. A user can load the reusable transmitter 155 into a new sterile tub assembly 100 using the steps discussed above. The user can then (a) load the new sterile tub assembly 100 with the reusable transmitter 155 and the new analyte sensor into the same inserter 1 that the user used for the previous analyte sensor and (b) follow the above-disclosed steps to attach and activate the new analyte sensor.

Some embodiments of the invention are also directed to a kit that includes the inserter, transmitter and sterile tub that includes the medical device (analyte sensor). Accordingly, because the transmitter and inserter are reusable, the cost of the body wearable medical device (analyte sensor), is reduced.

Figure 15:
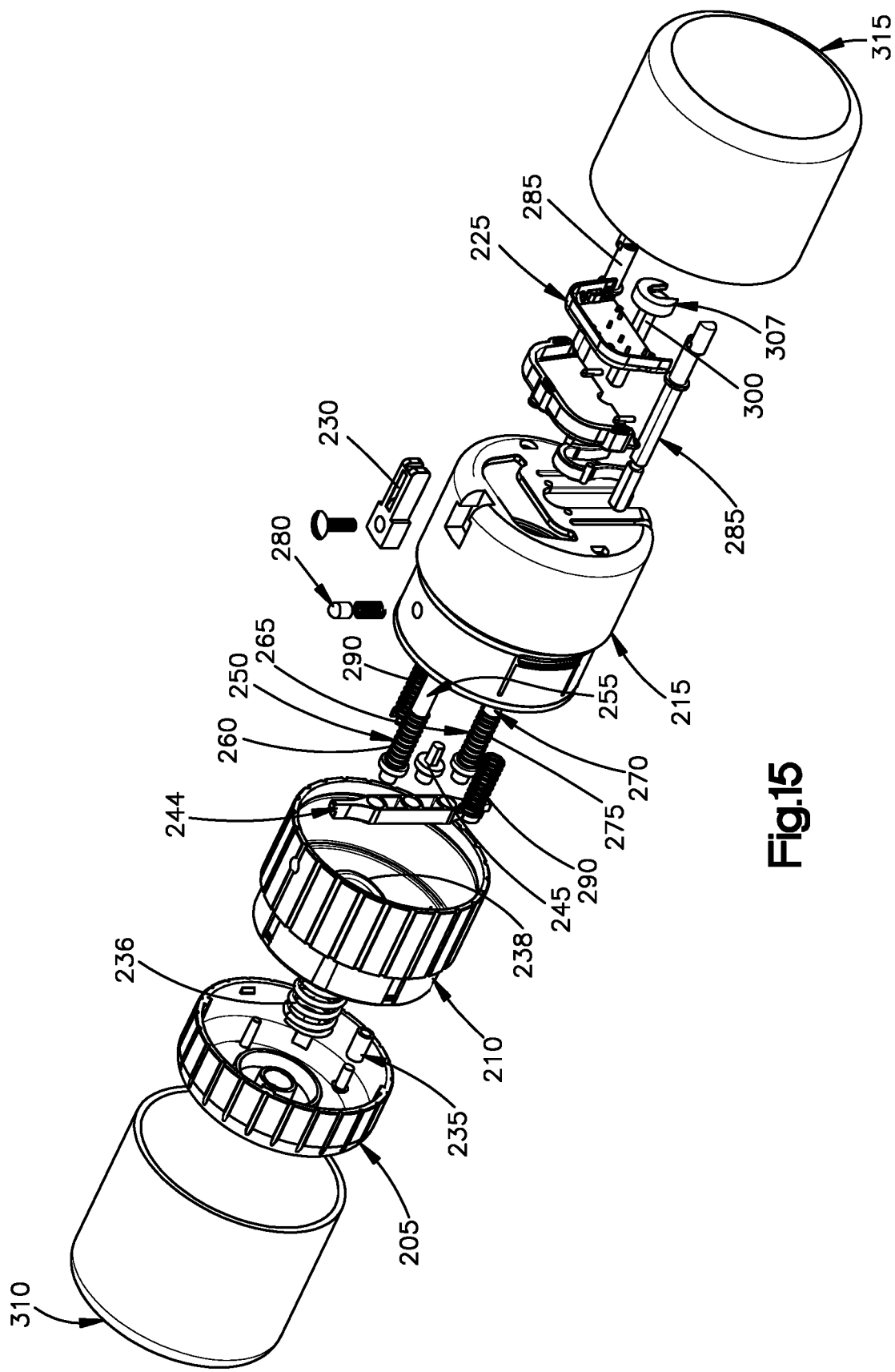
FIG. 15 is an exploded view of the inserter depicted in FIG. 14 showing the internal components of the inserter, according to an embodiment of the present invention.

Depicted in FIGS. 14-32 is another embodiment of the present invention. As can be seen in FIGS. 14-19, the inserter 200 includes a handle twist cam eject portion 205, an applicator handle twist cam portion 210, an applicator handle 215, a safety inserter/lancet shaft receiving slot 220, a transmitter holder 225 and a sterile tub positioning tab receiving slot 230. FIGS. 15 and 17 are exploded views of the inserter 200 depicted in FIG. 14 showing the internal components of the inserter 200. Included are the handle twist cam eject portion 205, push rod stubs 235, the applicator handle twist cam portion 210, an ejector cam spring 236, a plunger assembly cam 238 located on the interior of the applicator handle twist cam portion 210 (see FIG. 16), a plunger bridge 244, a lancet plunger coupling 245, a transmitter plunger assembly 250 that includes a transmitter plunger 255 and a transmitter plunger biasing element 260, which, in some embodiments, is a coiled compression spring, a guide shaft assembly 265 that includes a guide shaft 270 and a guide shaft biasing element 275, which, in some embodiments, is a coiled compression spring, a safety button 280, the applicator handle 215, the sterile tub positioning tab receiving slot 230, a pair of ejector bars 235 and ejector bar biasing elements 290, which, in some embodiments, is a coiled compression spring, transmitter holder 225, and a lancet plunger assembly 295 that includes a lancet plunger 300 and a lancet plunger biasing element 305, which, in some embodiments, is a coiled compression spring.

Figure 16:
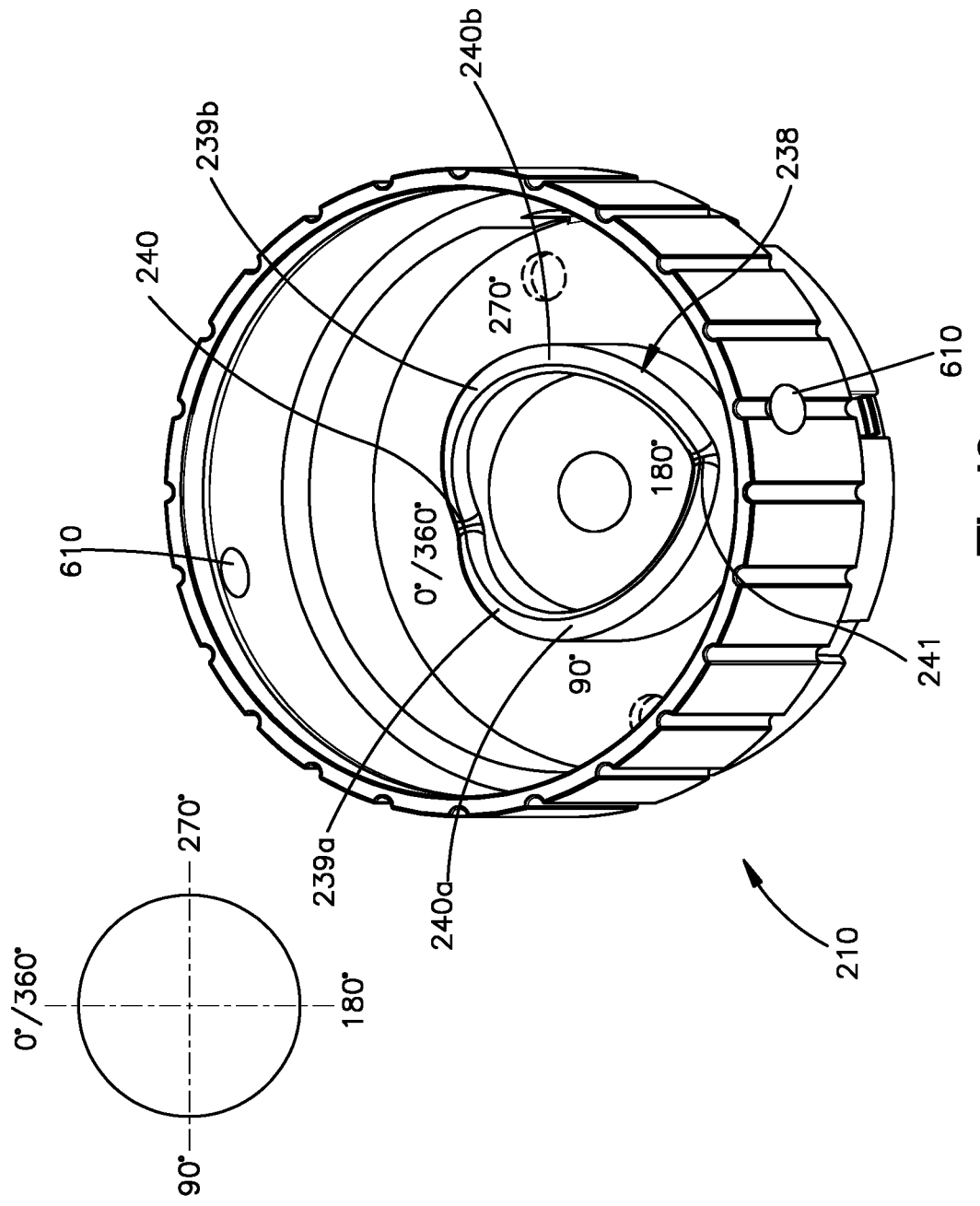
FIG. 16 is a perspective view the applicator handle twist cam portion depicted in FIG. 15 showing the internal construction of the applicator handle twist cam portion, according to an embodiment of the present invention.
Figure 17:
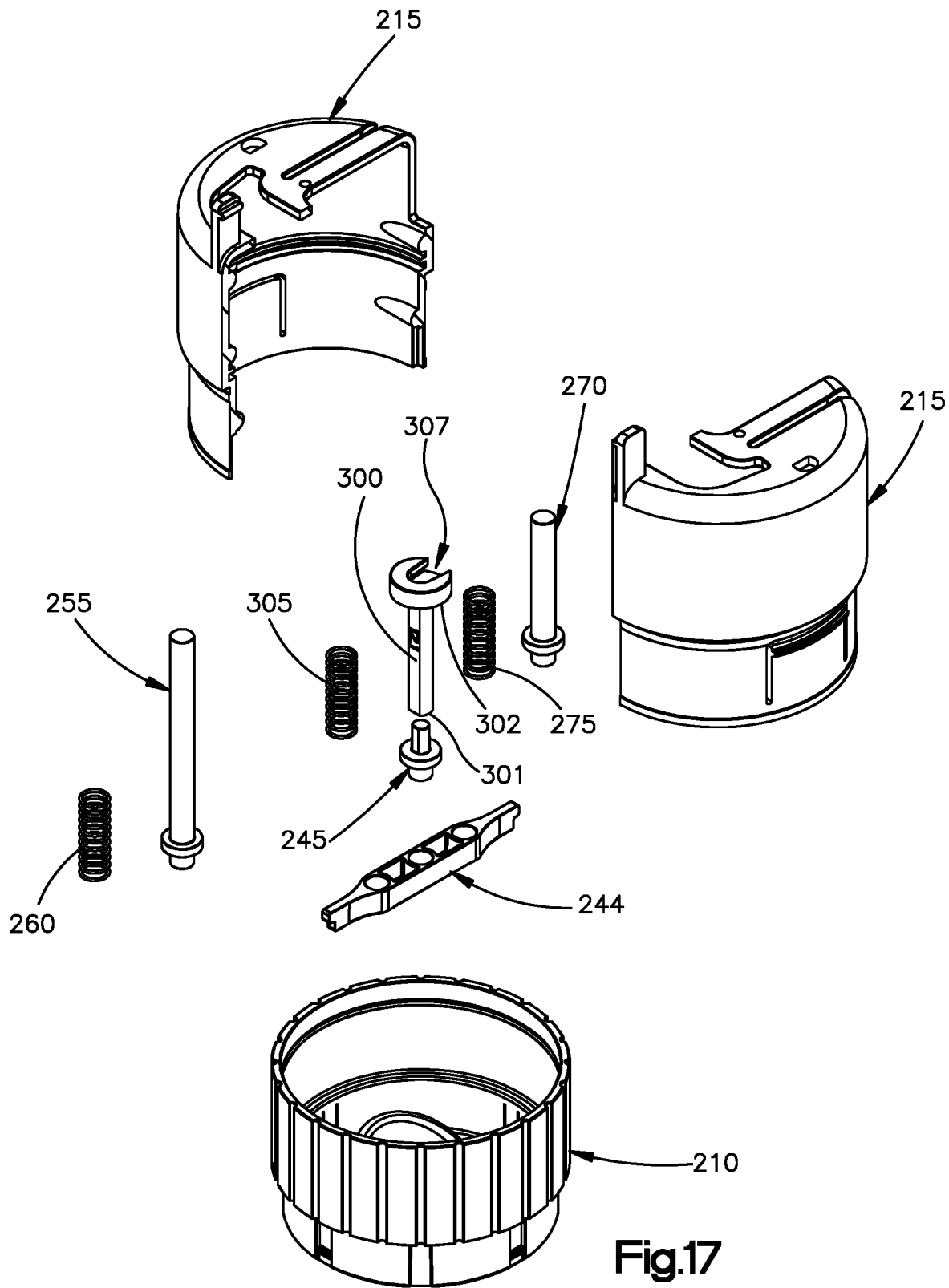
FIG. 17 is an exploded view of the inserter depicted in FIG. 14 showing the internal components of the inserter, according to an embodiment of the present invention.

Depicted in FIG. 16 is a magnified view of the plunger assembly cam 238 located on the interior of the applicator handle twist cam portion 210. As can be seen in the figure, the plunger assembly cam 238 includes two portions or lobes—a first portion/lobe 239a that extends from 0° to 180° and a second portion/lobe 239b that extends from 180° to 360°. Lobe 239a has a high point 240a at approximately 90° and lobe 239b has a high point 240b at approximately 270°. The plunger assembly cam 238 has a low point 240 at approximately 0° and a low point 241 at approximately 180°.

As can best be seen in FIGS. 15 and 17, a first end 301 of the lancet plunger 300 is configured to receive and mate with the lancet plunger coupling 245 and a second end of the lancet plunger 300 is configured to receive and mate with a lancet shaft flange portion of a lancet shaft of an analyte sensor (discussed in detail below). In some embodiments, the first end of the lancet plunger 300 includes a hollow central portion that receives a shaft portion of the lancet plunger coupling 245 and the second end of the lancet plunger 300 includes a keyed portion 307 that receives the lancet shaft flange portion to lock the lancet plunger and the lancet shaft together as discussed in detail below. In some embodiments, the inserter 200 includes a base cover 310 and/or an applicator cover 315.

Depicted in FIGS. 20-23 is an embodiment of a sterile tub assembly 350 that can be used with the inserter 200. The sterile tub assembly 350 includes a tub portion 355 that houses the components of a medical device, which in this embodiment is an analyte sensor. The tub portion 355 includes a first or sterile portion 360 that houses the sterile components of the analyte sensor and a second or non-sterile portion 365 that is a cavity having a removeable tub lid 370 to receive a reusable transmitter (discussed in more detail below) for the analyte sensor. Extending from the top of the of the tub portion 355 is a lancet shaft 375 that includes a lancet or other skin piercing element 377 that is used to transdermally deliver the subcutaneous portion of the analyte sensor. The lancet shaft 375 includes a flange portion 380 that is designed to be received within the lancet plunger 300 keyed portion 307 of the inserter to lock the lancet shaft 375 and the lancet plunger 300 together when the sterile tub assembly 350 is inserted into the inserter 200 as discussed below. The sterile tub assembly 350 also includes positioning tab 382 and a pair of locking cams 385 that are used to lock the analyte sensor in place within the sterile tub assembly 350 prior to use and to release the analyte sensor from the sterile tub assembly 350 during delivery of the analyte sensor by the inserter 200.

In use, the lancet shaft 375 is slideable within the tub portion 355 such that the lancet or other skin piercing element 377 can extend through the base 387 of the tub portion 355 and into a patient's skin during delivery and placement of the analyte sensor on a patient's skin by the inserter 200. In order to prevent inadvertent movement/sliding of the lancet shaft 375 and penetration of the lancet or other skin piercing element 377 through the base 387 of the tub portion 355 and possible injury to a user/patent, the sterile tub assembly 350 includes an inserter safety tab 390. As depicted in FIGS. 20-23, the inserter safety tab 390 includes (a) a locking arm 400 having an engaging portion 410 that engages the lancet shaft 375 and locks the lancet shaft 375 in a stationary position thereby preventing movement of the lancet shaft 375 while the inserter safety tab 390 is in place, (b) a tub engaging portion 412 that clips onto and engages the tub portion 355 and (c) a grasping portion 414 that allows a user to grab onto in order to remove the inserter safety tab 390 prior to use.

In some embodiments, the engaging portion 410 is "U" shaped with a width "W" that is wider than the diameter of at least a portion of the lancet shaft 375 in order to receive the lancet shaft 375 therein. As can be seen in the figures, the lancet shaft 375 includes a locking portion 415 adjacent to the engaging portion 410 of the inserter safety tab 390 that is wider than or has a diameter that is greater than the width "W" of the engaging portion 410. Thus, when the inserter safety tab 390 is in place on the sterile tub assembly 350, the engaging portion 410 abuts the locking portion 415 and prevents the lanset shaft 375 from moving through the engaging portion 410 of the locking arm 400 thereby locking the lancet shaft 375 in a stationary position. As will be readily understood by those of skill in the art, many different safety inserter tab designs may be used so long as the safety inserter tab prevents movement of the lancet shaft while the safety inserter tab is in place on the sterile tub assembly and that allows movement of the lancet shaft when the safety inserter tab is removed from the sterile tub assembly.

Figure 28A:
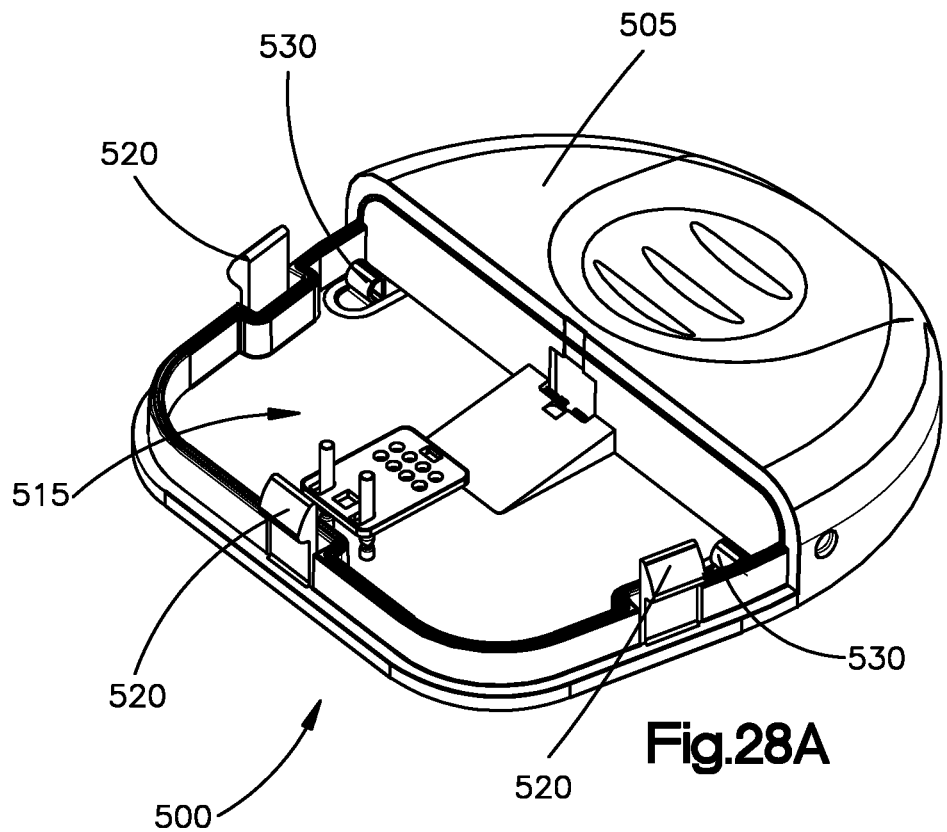
FIGS. 28A-28B depict perspective views of an analyte sensor without a transmitter attached thereto, according to an embodiment of the present invention.
Figure 28B:
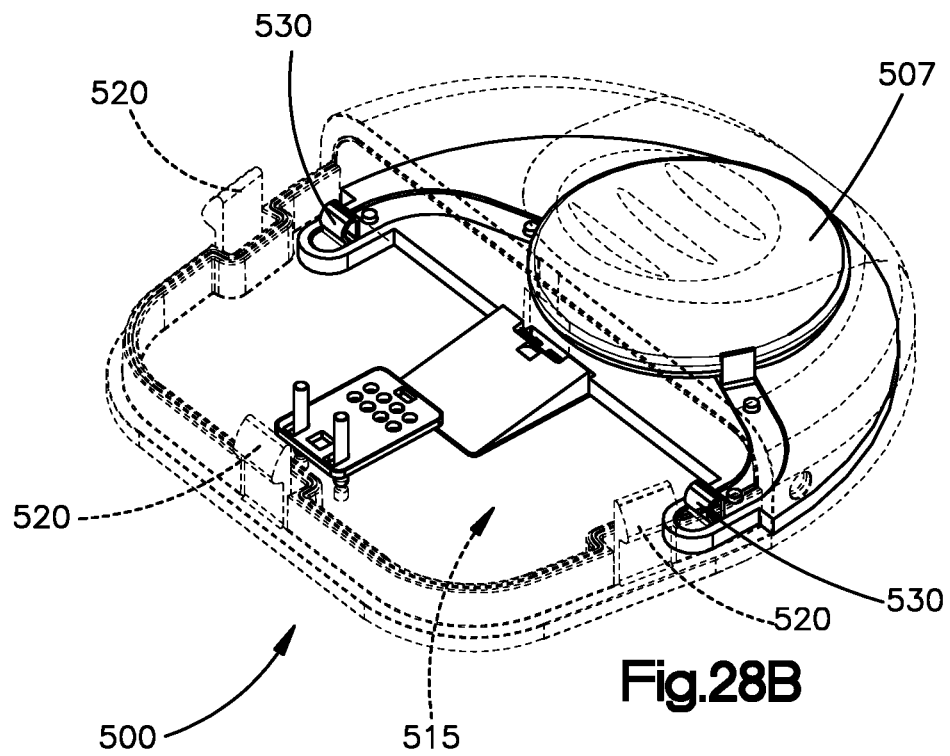

Depicted in FIGS. 24-28 is an embodiment of an analyte sensor 500 that can be used with the inserter 200. The analyte sensor 500 includes a sterile or first portion 505 that houses many of the components of the sensor including the battery 507, etc. and excluding the transmitter 510, and a transmitter or second portion 515 that receives/houses the transmitter 510, which may or may not be reusable. A plurality of attachment elements 520 such as, for example, clips, may also be included to secure the transmitter 510 to the transmitter or second portion 515 of the analyte sensor 500. An adhesive pad 525 is attached/adhered to the bottom of the analyte sensor 500 and/or tub portion 355 of the sterile tub assembly 350 in such a manner that (a) sterility is maintained for the sterile or first portion 505 of the analyte sensor 500 and (b) the adhesive pad 525 detaches from the tub portion 355 and remains attached to the analyte sensor 500 after the inserter 200 applies the analyte sensor 500 to the skin of a patient as described below. As can be seen in FIG. 28, the analyte sensor 500 includes at least one battery contact 530, and preferably two battery contacts 530, located in the transmitter or second portion 515. Thus, when the transmitter is fully inserted into the transmitter or second portion 515, these battery contacts 530 contact associated battery contacts 221 on the transmitter 510 thereby activating the transmitter 510 and hence, the analyte sensor 500, for use.

Use and operation of the inserter 200 according to an embodiment of the invention will now be described in detail. In some embodiments, the sterile tub assembly 350 will be preloaded with the analyte sensor 500 in the sterile or first portion 360 of the tub portion 355. Prior to attaching the sterile tub assembly 350 to the inserter 200, as depicted in FIGS. 29A and 29B, the transmitter 510 is inserted "upside down" and "clipped" into the transmitter holder 225 on the inserter 200 such that the battery contacts 221 are exposed to the sterile tub assembly 350. After the transmitter 510 is in place, the sterile tub assembly 350 can now be added/attached to the inserter 200.

Figure 30:
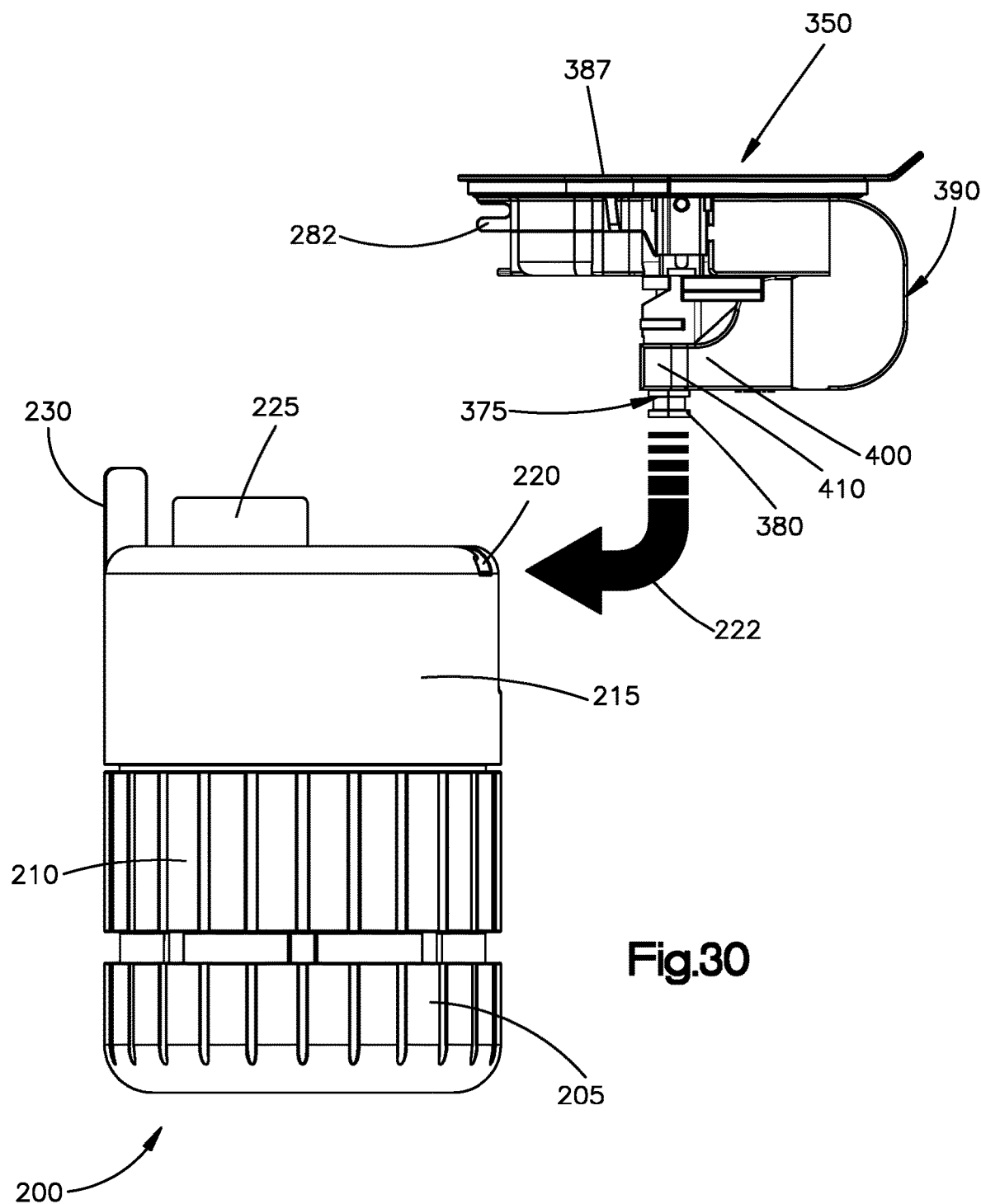
FIG. 30 depicts the process for attaching a sterile tub assembly to an inserter, according to an embodiment of the present invention.
Figure 31:
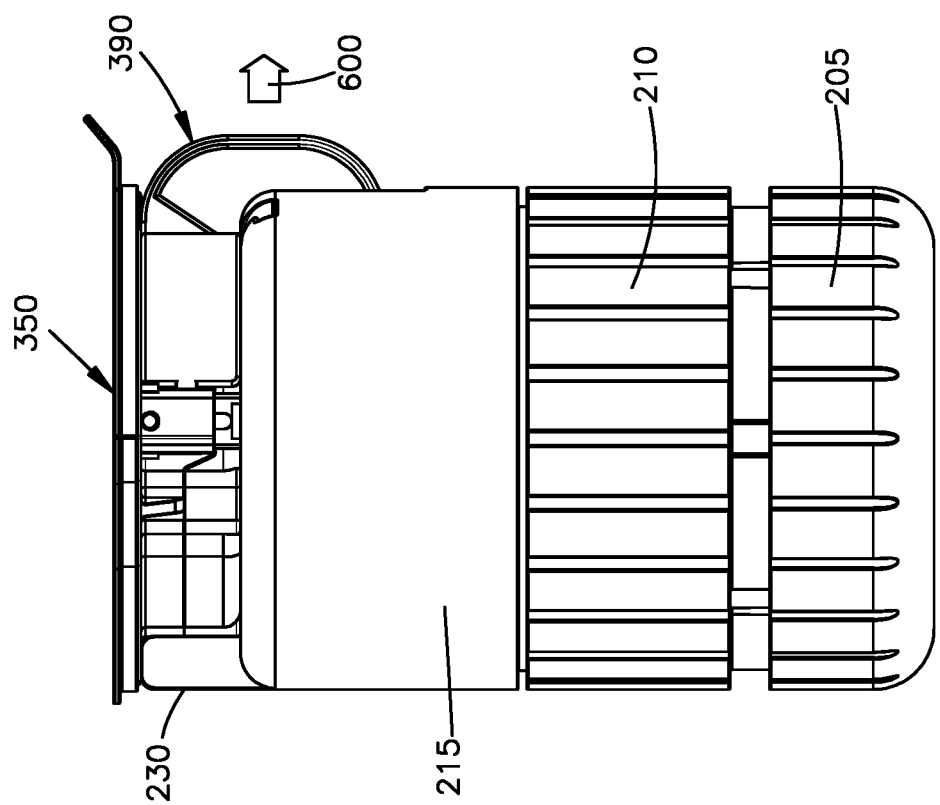
FIG. 31 is a side view of an inserter with a sterile tub assembly fully attached thereto, according to an embodiment of the present invention.

With the transmitter 510 in place and the tub lid 370 removed from the sterile tub assembly 350, as depicted in FIG. 30, holding the sterile tub assembly 350 "upside down" in one hand while holding the inserter 200 in the other hand, a user slides/inserts the lancet shaft 375 with the attached inserter safety tab 390 of the sterile tub assembly 350 into the safety inserter/lancet shaft receiving slot 220 on the inserter 200 as indicated by arrow 222. FIG. 31 depicts the inserter 200 with a fully and properly inserted sterile tub assembly 350.

Figure 18:
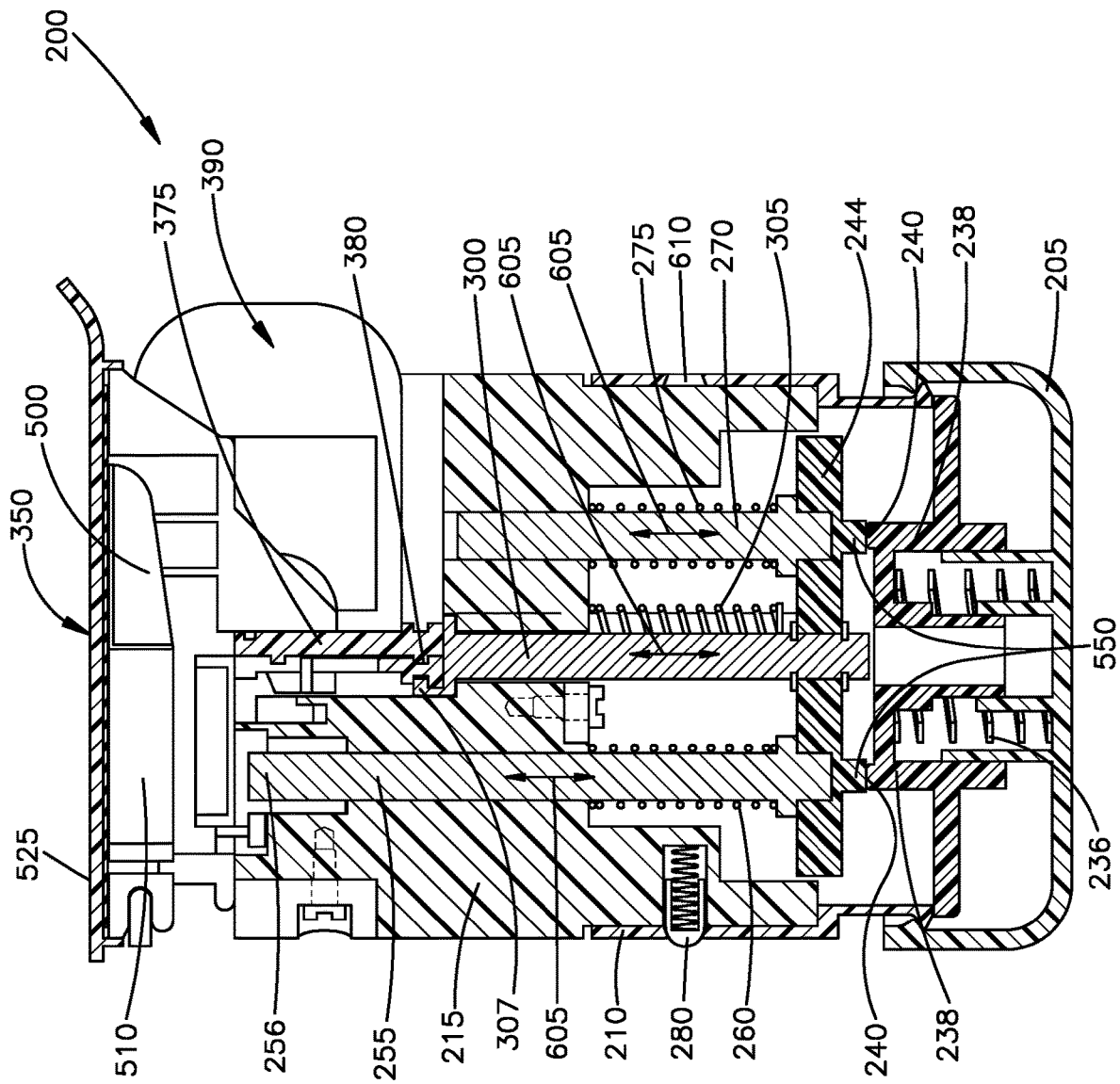
FIG. 18 is a side view of the inserter depicted in FIG. 14 showing the internal components of the inserter in an un-actuated state, according to an embodiment of the present invention.
Figure 19:
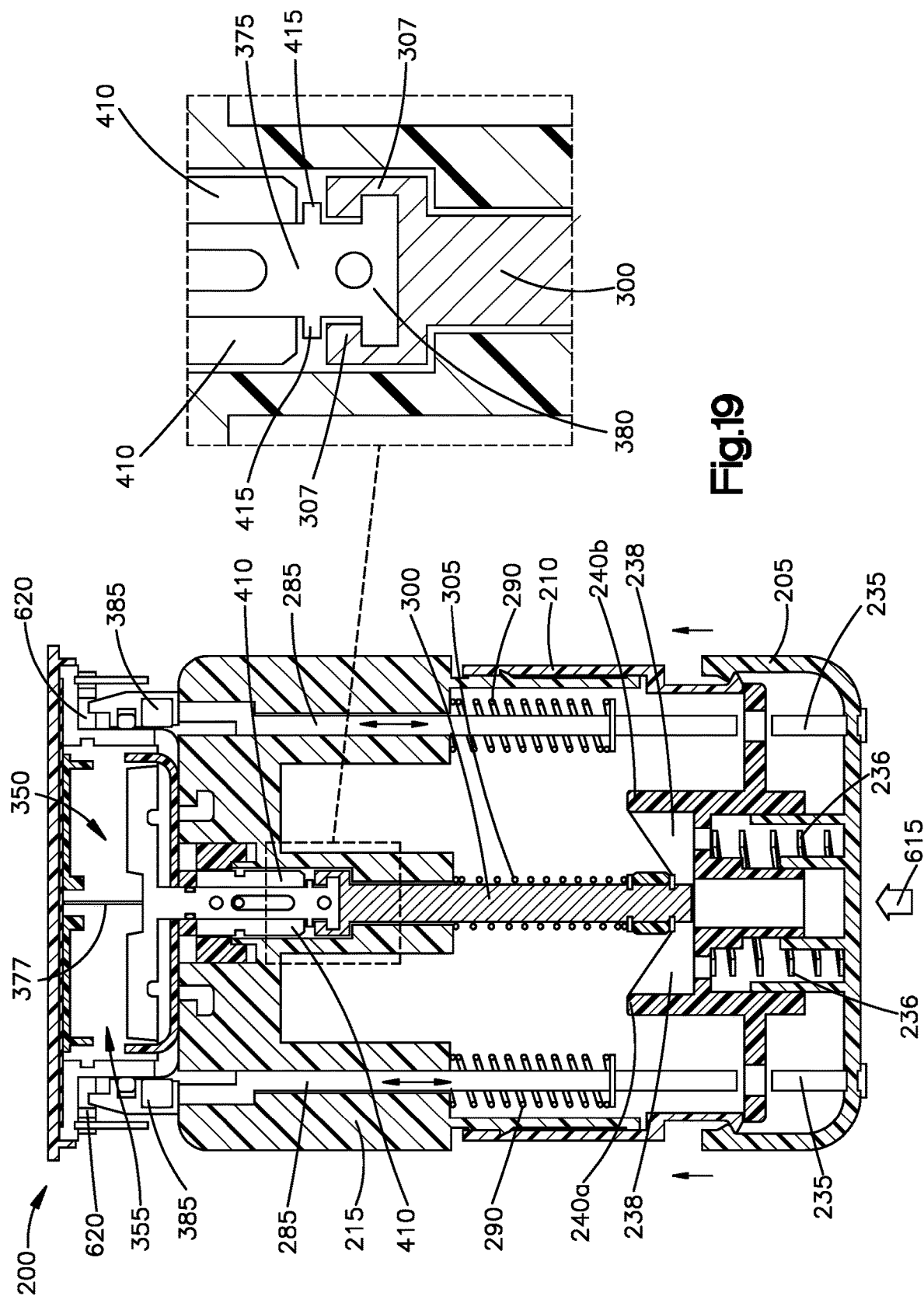
FIG. 19 is a front view of the inserter depicted in FIG. 14 showing the internal components of the inserter in an un-actuated state, according to an embodiment of the present invention.
Figure 20:
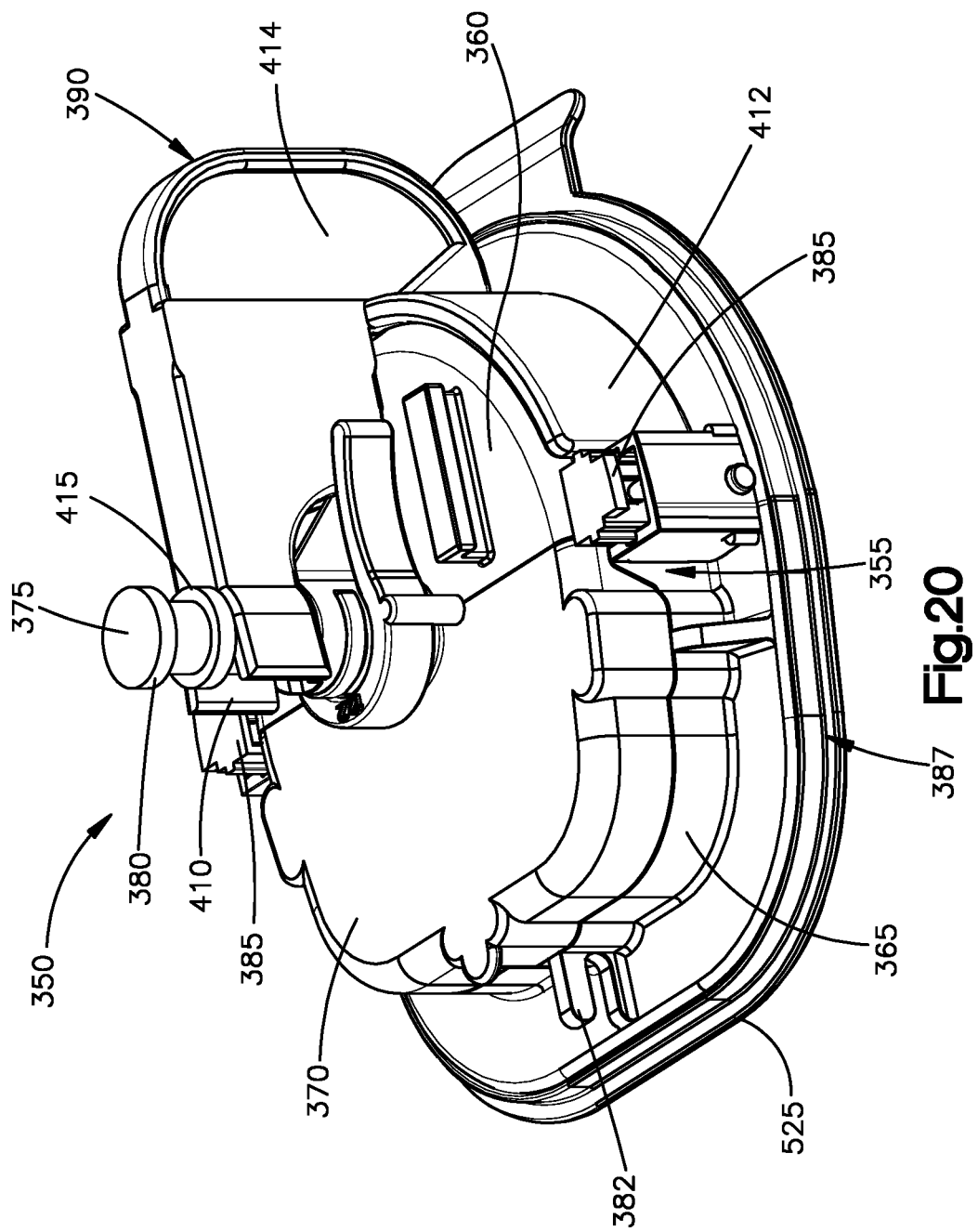
FIG. 20 is a perspective view of a sterile tub assembly, according to an embodiment of the present invention.

Sliding/inserting the sterile tub assembly 350 into the safety inserter/lancet shaft receiving slot 220 from the side allows the positioning tab 382 to be received within the sterile tub positioning tab receiving slot 230, the transmitter 510 to be received within the second or non-sterile portion 365 of the tub portion 355 and the flange portion 380 of the lancet shaft 375 to be received within the lancet plunger 300 keyed portion 307. As depicted in FIGS. 18 and 19, when properly inserted, the flange portion 380 of the lancet shaft 375 is received within the lancet plunger 300 keyed portion 307 such that the lancet shaft 375 and lancet plunger 300 are "locked" together. As depicted in FIG. 18, when the sterile tub assembly 350 is fully inserted into the safety inserter/lancet shaft receiving slot 220 of the inserter 200, a distal end 256 of the transmitter plunger 255 is adjacent to the transmitter 510 included in the tub portion 355. As can be seen in FIGS. 18 and 19, which are side and front views, respectively, of the inserter 200/sterile tub assembly 350 combination depicting the internal components, prior to inserter 200 activation, the transmitter plunger 255, guide shaft 270 and lancet plunger 300 are positioned on low points 240, 245 of the plunger assembly cam 238 by way of the plunger bridge 244. In some embodiments, cam contact nubs 550 are included on the bottom of the plunger bridge 244. In use, these cam contact nubs 550 slide/ride along the cam lobes 239a, 239b as the applicator handle twist cam portion 210 and applicator handle 215 are rotated relative to one another as discussed below.

The inserter 200 is now ready to (a) activate the analyte sensor 500 for use, (2) attach the analyte sensor 500 to skin and (c) transdermally deliver the sensing element of the analyte sensor 500.

Initially, the adhesive backing is removed from the adhesive pad 525 pad to expose the adhesive used to adhere the adhesive pad 525 and hence, the analyte sensor 500, to a patient's skin. Next, the user or caregiver selects a location on the body for sensor placement and with the inserter 200 in hand, presses the adhesive pad 525 against the patient's skin at the preferred body location. The user should apply a circular pressing motion to ensure that the adhesive pad 525 is properly adhered to the skin. After the adhesive pad 525 is adhered to the skin, the user removes the inserter safety tab 390 by pulling it laterally away from the inserter 200 as indicated by arrow 600 in FIG. 31 thereby unlocking the lancet shaft 375. The user then depresses the safety button 280 on the applicator handle twist cam portion 210 to unlock the applicator handle twist cam portion 210 and applicator handle 215 from each other and twists/rotates the applicator handle twist cam portion 180° relative to the applicator handle 215.

As previously disclosed, included on the interior of the applicator handle twist cam portion 210 is a plunger assembly cam 238. Thus, as the applicator handle twist cam portion 210 is rotated relative to the applicator handle 215, the bottom of the plunger bridge 244 that contacts the cam lobes 239a, 239b (cam contact nubs 550 in some embodiments) on the plunger assembly cam 238, ride/slide along the cam lobes 239a, 239b causing the plunger bridge 244 and the attached transmitter plunger 255, guide shaft 270 and lancet plunger 300 to move up and down in a linear motion towards and away from the sterile tub assembly 350 (as indicated by arrows 605 in FIG. 18) in a manner that corresponds to the profile of the cam lobes 239a, 239b. In some embodiments, the profile of the cam lobes 239a, 239b, causes the plunger bridge 244 and the attached plungers/shafts to move towards the sterile tub assembly approximately 6.5 mm. As will be readily understood by those of skill in the art, the distance that the plunger bridge 244 travels can be controlled by the profile of the cam lobes 239a, 239b.

Figure 23:
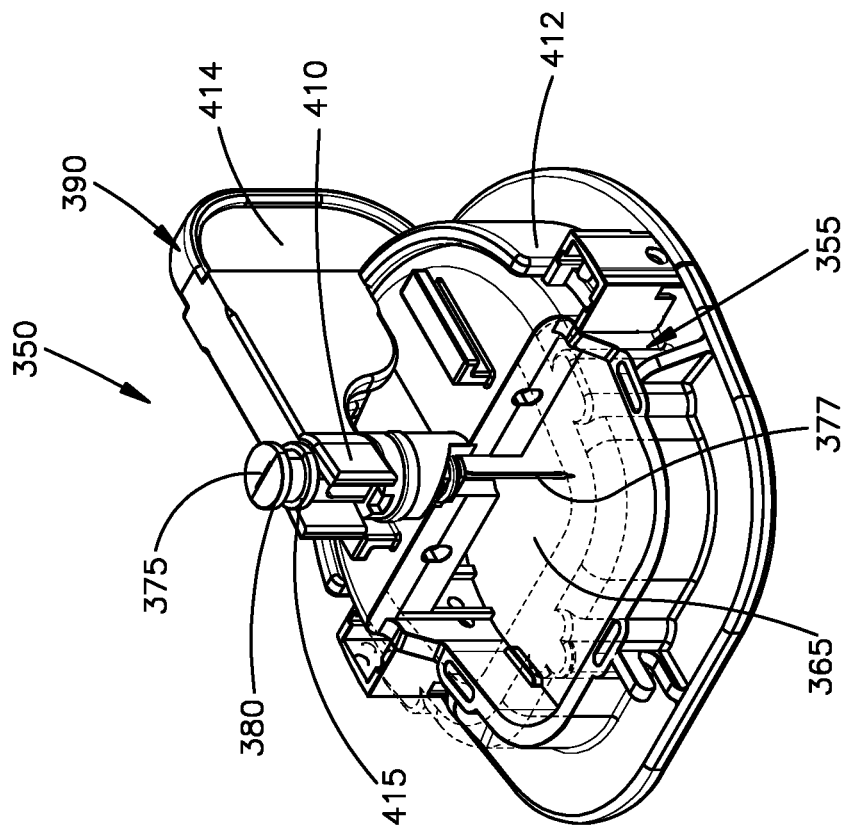
FIG. 23 is a perspective view of a sterile tub assembly, according to an embodiment of the present invention.
Figure 22:
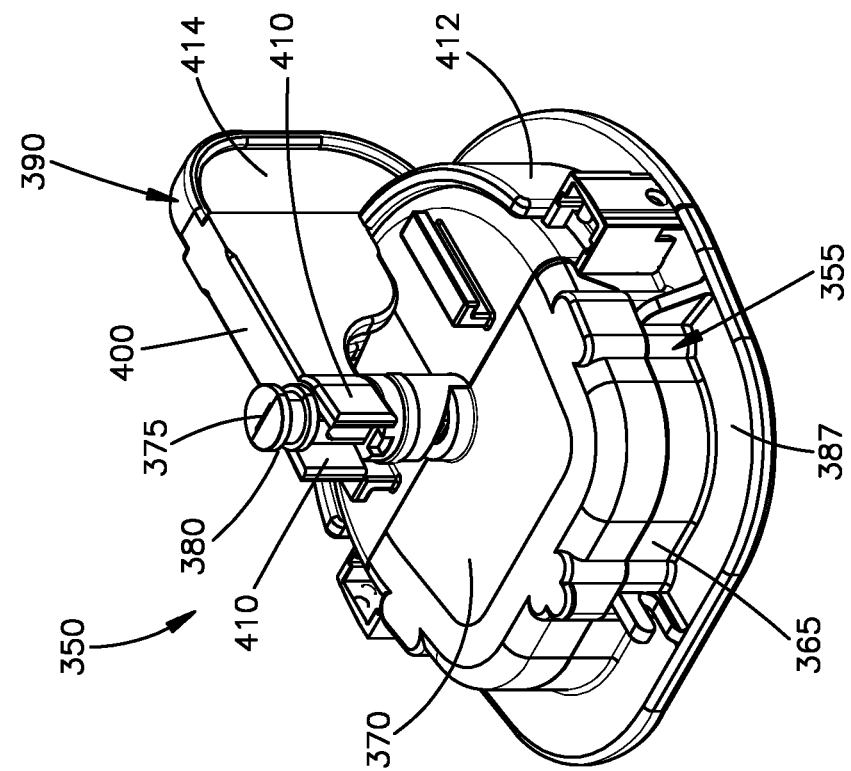
FIG. 22 is a perspective view of a sterile tub assembly, according to an embodiment of the present invention.
Figure 25:
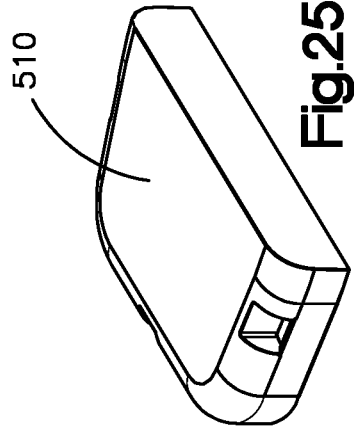
FIG. 25 is a perspective view of a transmitter for use with the analyte sensor depicted in FIG. 24, according to an embodiment of the present invention.
Figure 27:
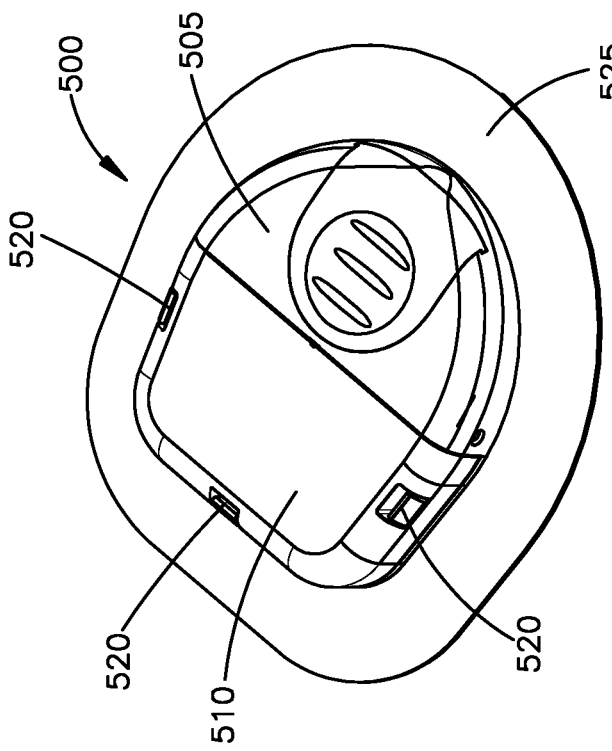
FIG. 27 is a perspective view of an analyte sensor with the transmitter attached thereto, according to an embodiment of the present invention.
Figure 24:
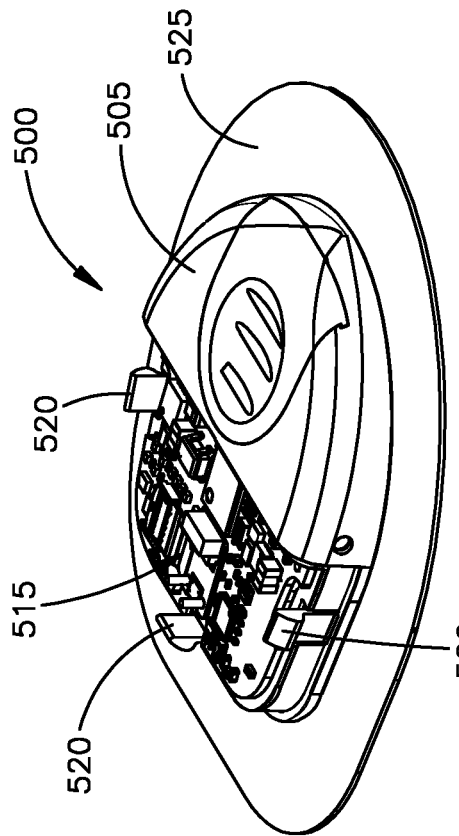
FIG. 24 is a perspective view of an analyte sensor without a transmitter attached thereto, according to an embodiment of the present invention.
Figure 26:
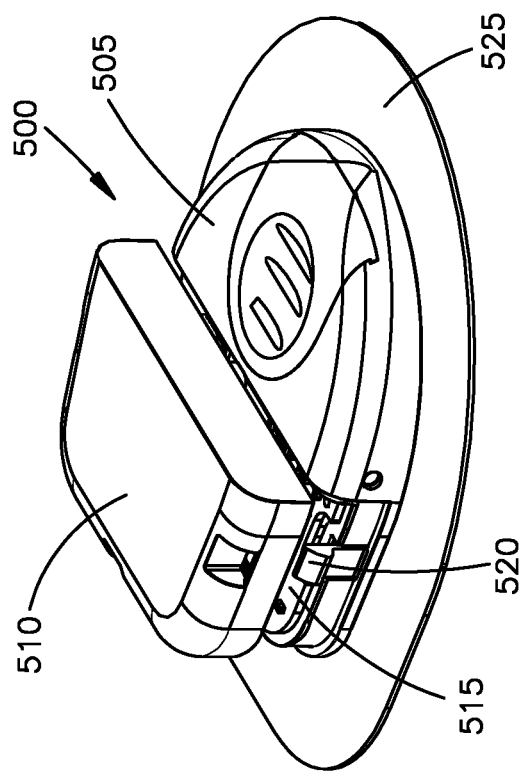
FIG. 26 is a perspective view of an analyte sensor showing attachment of a transmitter thereto, according to an embodiment of the present invention.

As can be seen in FIGS. 21 and 23, the lancet shaft 375 is connected to a lancet 377, which is attached to the sensing element of the analyte sensor 500 that is to be delivered transdermally. Accordingly, as the applicator handle twist cam portion 210 is rotated relative to the applicator handle 215 and the plunger bridge 244 slides along the cam lobes 239a, 239b from the low points 240, 241 to the high points

240a, 240b, the lancet plunger 300 and the connected lancet shaft 375, lancet 377 and sensing element move linearly towards the sterile tub assembly 350 a max distance of approximately 6.5 mm. Movement of the lancet shaft 375, lancet 377 and sensing element this distance causes the lancet 377 and sensing element to pierce and move through a sealed silicon membrane in the base of the analyte sensor 500 and through the adhesive pad 525. The lancet 377 then pierces the patient's skin thereby inserting the sensing element transdermally.

Because the transmitter plunger 255 is also attached to the plunger bridge 244, this movement of the plunger bridge 244 also causes the transmitter plunger 255 to move a corresponding distance thereby pushing the transmitter 510 that has been loaded into the transmitter holder 225 on the inserter 200 is place onto the back of the analyte sensor 500. As the transmitter 510 is pushed into its working position by the transmitter plunger 255, attachment elements 520 on the transmitter or second portion 515 of the analyte sensor, secure the transmitter 510 in place. When secured in place, the battery contacts 221 on the transmitter 510 and the battery contacts 530 on the analyte sensor 500 align and make contact thereby activating the transmitter 510 and hence, the analyte sensor 500, for use. The points on the cam lobes 239a, 239b when (a) the lancet 377 and attached sensing element are delivered a max distance into the skin and (b) the transmitter 510 is attached to the analyte sensor 500 and activated, correspond to high points 240a and 240b, as depicted in FIG. 16, and correspond to a relative rotation of the applicator handle twist cam portion 210 to the applicator handle 215 of approximately 90°. Additionally, at this point of rotation, the transmitter plunger biasing element 260 and the lancet plunger biasing element 305 are compressed a distance equal to the travel distance of the plunger bridge 244 thereby loading the biasing elements 260, 305 with stored energy.

As the user continues to rotate the applicator handle twist cam portion 210 and the associated plunger assembly cam 238 through the next approximately 90°, the plunger bridge 244 slides along the cam lobes 239a, 239b from the high points 240a, 240b to the low points 240, 241 causing (a) the transmitter plunger 255 and (b) the lancet plunger 300 and the connected lancet shaft 375 and lancet 377 to retract as well. Retraction of the transmitter plunger 255 and the lancet plunger 300 is aided by the biasing elements 260, 305 unloading their stored energy. As the lancet 377 is retracted from the patient's skin, the sensing element detaches from the lancet 377 and is left implanted in place within the patient's skin.

Thus, based on the profile of the cam lobes 239a, 239b, rotating the applicator handle twist cam portion 210 through the first approximately 90° causes the shape/profile of the plunger assembly cam 238 to move the plunger bridge 244 and the attached transmitter plunger 255 and lancet plunger 300 to attach the transmitter 510 to the analyte sensor 500 and to deliver the lancet 377 and the attached sensing element transdermally and rotating the applicator handle twist cam portion 210 through the second approximately 90° causes the shape/profile of the plunger assembly cam 238 to move the plunger bridge 244 and the attached transmitter plunger 255 and lancet plunger 300 to retract (a) removing the transmitter plunger 255 from the tub portion 355 and (b) retracting the lancet 377 from the skin, leaving the sensing element implanted. Upon a completed 180° degree rotation of the applicator handle twist cam portion 210, an audible "click" will sound signifying that the safety button 280 has popped out of the hole 610 on the opposite side of the applicator handle twist cam portion 210. This indicates that the lancet 377 (a) has fully implanted the sensing element and (b) has fully retracted to a "safe" position within the tub portion 355, and as a result, the inserter has performed a completed delivery cycle.

In order to eject the analyte sensor 500 from the tub portion 355 to remove the inserter 200 leaving the analyte sensor 500 attached to the patient's skin, the user applies pressure substantially perpendicular to the patient's skin as indicated by arrow 615 in FIG. 19, to the handle twist cam eject portion 205. This action causes the handle twist cam eject portion 205 to move relative to the applicator handle twist cam portion 210 towards the patient's skin. This movement causes the push rod stubs 235 to engage the ejector bars 285 and push the ejector bars 285 forward towards the patient's skin. As the ejector bars 285 move forward, they engage and push the locking cams 385 forward, which pull a pair of analyte sensor locking pins 620 back thereby releasing the analyte sensor 500 from the tub portion 355. The user can now remove the inserter 200 from the skin leaving the analyte sensor 500 in place and attached to the skin while the sterile tub assembly 350 remains attached to the inserter 200. Once pressure is removed from the inserter 200, the ejector cam spring 236 returns the handle twist cam eject portion 205 back to its starting position. The ejector bar springs 290, which are attached to the ejector bars 285, return the ejector bars back to their starting position. To remove the used sterile tub assembly 350 from the inserter 200, the user can apply pressure with their fingers to the bottom of the sterile tub assembly 350 to slide the sterile tub assembly 350 off of the inserter 200 in a manner opposite to how the sterile tub assembly 356 was attached to the inserter 200.

The lancet 377 is retained within the sterile tub assembly 350 in a retracted and locked "safe" position to prevent injury to the user or any other person. The used sterile tub assembly 350 can then be disposed of safely and in an environmental manner in, for example, a "sharps" or "needle safe" container.

Figure 32:
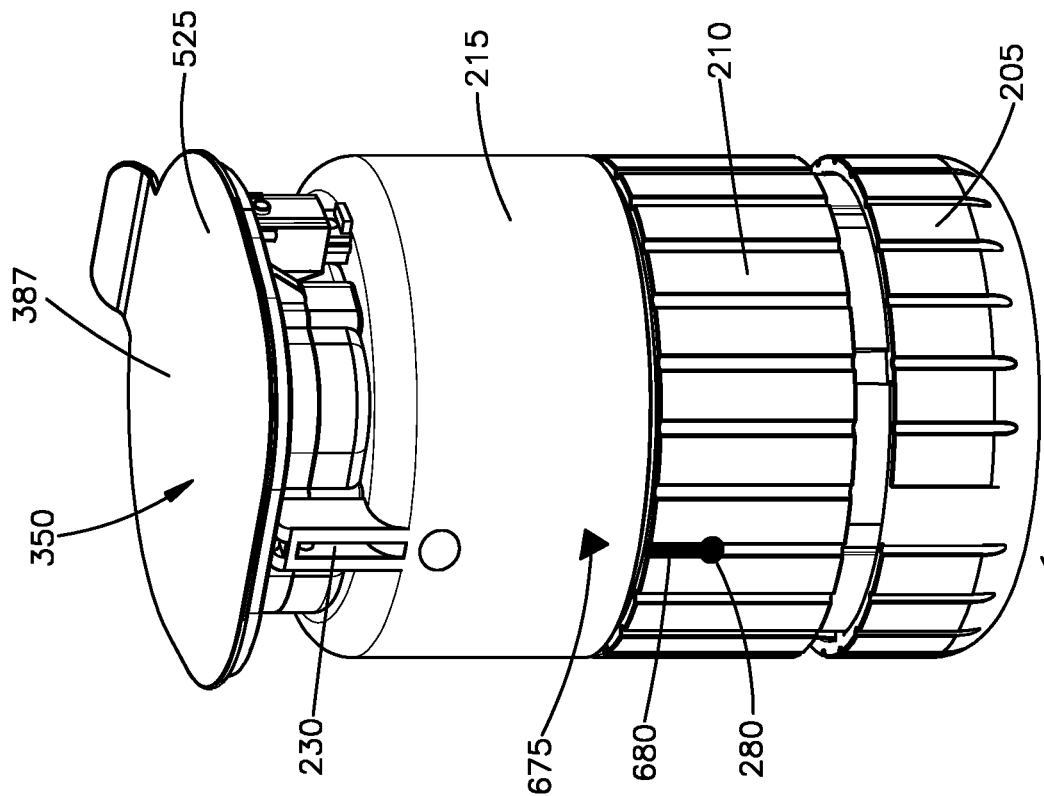
FIG. 32 is a perspective view of the inserter and sterile tub assembly depicted in FIG. 32, according to an embodiment of the present invention.

In order to reuse the inserter after a completed delivery and application of an analyte sensor to the skin, the user holds the applicator handle 215 with one hand and depresses the safety button 280 with the other hand. The user then rotates the applicator handle twist cam portion 210 back to its starting position, i.e., 180°, where the safety button 280 "pops" back out of the hole located 180° degrees on the opposite side of the applicator handle twist cam portion 210. As depicted in FIG. 32, in some embodiments, the "start" position is indicated by an arrow or other marking 675 on the applicator handle 215 and a line or other marking 680 on the applicator handle twist cam portion 210.

The analyte sensor 500 now activated and attached to the patient's skin by way of the adhesive pad 525 can be used for approximately two (2) weeks after which, the patient can remove the analyte sensor 500 from the skin by peeling the adhesive pad 525 off of the skin. Removing the analyte sensor also removes the sensing element from the patient's skin. Once the analyte sensor 500 is removed, the user can remove the reusable transmitter 510 from its clipped-on location on the analyte sensor 500. The used analyte sensor 500 can then be disposed of safely by the user and the reusable transmitter 510 can be inserted into the transmitter holder 225 of the inserter 200 for use with a new analyte sensor 500. The user can then (a) load the new sterile stub assembly 350 with the new analyte sensor into the same inserter 200 that the user used for the previous analyte sensor and (b) follow the above-disclosed steps to attach and activate the new analyte sensor.

Some embodiments of the invention are also directed to a kit that includes the inserter, transmitter and sterile tub assembly that includes the medical device (analyte sensor). Accordingly, because the transmitter and inserter are reusable, the cost of the body wearable medical device (analyte sensor), is reduced.

In some embodiments, the inserters disclosed and described herein may be available in a package that may initially contain the inserter, the reusable transmitter and the sterile tub assembly that includes the medical device (analyte sensor) preloaded therein. For subsequent uses of the inserter, a user can purchase new sterile tub assemblies that include the medical device (analyte sensor) preloaded therein.

As will be readily understood by those of skill in the art, embodiments of the disclosed and described inserters and sterile tubs can be designed to use a lancet or other skin piercing element to transdermally deliver other components of a medical device such as, for example, drug delivery cannulas (micro catheters) or other delivery lumens for infusion pumps to deliver, for example, insulin and other therapeutic agents/treatments to a patient. In addition, lancet and other skin piercing elements can be used with the disclosed and described inserter and sterile tub embodiments to implant drug eluting implants.

What is claimed:

1. An insertion system for a medical device, the insertion system comprising:
    an inserter comprising:
        a housing having a first end with an opening therein;
        an actuator;
        a cam member operably connected to the actuator;
        a cam bridge follower in contact with the cam member;
        a first plunger in contact with the cam bridge follower; and
    a tub assembly configured to be attached to the inserter, the tub assembly comprising:
        a tub portion including a first portion capable of holding a first component of the medical device and a second portion capable of holding a second component of the medical device; and
        a second plunger and a skin piercing element attached to the second plunger,
    wherein actuation of the actuator causes linear movement of the first plunger and the second plunger,
    wherein linear movement of the second plunger deploys the first component of the medical device and linear movement of the first plunger acts on the second component of the medical device.

2. The insertion system of claim 1, wherein the tub assembly is inserted into the opening in the first end of the housing.

3. The insertion system of claim 1, wherein the medical device is an analyte sensor.

4. The insertion system of claim 3, wherein the analyte sensor measures an analyte comprising glucose, galactose, fructose, lactate, peroxide, cholesterol, amino acids, alcohol, lactic acid, or mixtures of the foregoing.

5. The insertion system of claim 4, wherein movement of the cam bridge follower moves the first plunger and the second plunger in a corresponding manner.

6. The insertion system of claim 5, wherein movement of the cam bridge follower a maximum distance in a first direction results in the skin piercing element piercing a base of the tub assembly.

7. The insertion system of claim 6, wherein the skin piercing element is a lancet.

8. The insertion system of claim 1, wherein the actuator comprises a trigger, and wherein when pulled, the trigger causes rotation of the cam member.

9. The insertion system of claim 8, wherein the trigger is operationally connected to the cam member by a gear assembly.

10. The insertion system of claim 8, wherein the inserter further comprises a trigger spring configured to return the trigger to a starting position.

11. The insertion system of claim 1, wherein when the tub assembly is attached to the inserter, the cam bridge follower is in contact with the first plunger and the second plunger.

12. The insertion system of claim 1, wherein the inserter is reusable.

13. The insertion system of claim 1, wherein the actuator is capable of retracting the skin piercing element.

14. The insertion system of claim 1, wherein the actuator comprises a twist handle.

15. The insertion system of claim 1, wherein the tub assembly further comprises a safety tab that prevents movement of the skin piercing element when the safety tab is engaged.

16. The insertion system of claim 1, further comprising a safety button that locks the actuator until the safety button is depressed.

17. The insertion system of claim 16, wherein when the safety button is popped out, the safety button indicates that the skin piercing element is retracted into the tub portion.

* * * * *